US008679454B2

(12) United States Patent  
Guire et al.

(10) Patent No.: US 8,679,454 B2
(45) Date of Patent: *Mar. 25, 2014

(54) PARTICLE IMMOBILIZED COATINGS AND USES THEREOF

(75) Inventors: Patrick E. Guire, Eden Prairie, MN (US); Kristin S. Taton, Little Canada, MN (US); John V. Wall, Woodbury, MN (US)

(73) Assignee: Surmodics, Inc., Elden Prairie, MN (US)

( * ) Notice: Subject to any disclaimer, the term of this patent is extended or adjusted under 35 U.S.C. 154(b) by 329 days.

This patent is subject to a terminal disclaimer.

(21) Appl. No.: 12/383,762

(22) Filed: Mar. 27, 2009

(65) Prior Publication Data

US 2009/0186070 A1   Jul. 23, 2009

Related U.S. Application Data

(63) Continuation of application No. 10/261,110, filed on Sep. 30, 2002, now Pat. No. 8,158,106.

(60) Provisional application No. 60/327,441, filed on Oct. 5, 2001.

(51) Int. Cl.
*A61K 51/00* (2006.01)
*A61M 36/14* (2006.01)

(52) U.S. Cl.
USPC ......... 424/1.29; 424/1.11; 424/1.65; 424/9.6; 424/400; 424/489; 424/490

(58) Field of Classification Search
USPC ........... 424/1.11, 1.29, 1.33, 1.37, 1.49, 1.53, 424/1.57, 1.65, 1.69, 1.73, 9.1, 9.2, 9.3, 9.4, 424/9.5, 9.6, 9.7, 9.8, 400, 422, 423, 424, 424/425, 426, 484, 485, 486, 488, 489, 490, 424/491, 493, 494, 495, 496, 497, 499, 500, 424/501; 600/1, 2, 3, 4, 5, 6, 7, 8
See application file for complete search history.

(56) References Cited

U.S. PATENT DOCUMENTS

| | | | |
|---|---|---|---|
| 4,542,539 A | 9/1985 | Rowe, Jr. et al. | |
| 5,002,582 A | 3/1991 | Guire et al. | |
| 5,290,271 A | 3/1994 | Jernberg | |
| 5,348,873 A | 9/1994 | Matsuda et al. | |
| 5,470,307 A * | 11/1995 | Lindall | 604/20 |
| 5,558,854 A | 9/1996 | Quay | |
| 5,563,056 A | 10/1996 | Swan et al. | |
| 5,571,531 A | 11/1996 | McDermott et al. | |
| 5,645,593 A | 7/1997 | Woods et al. | |
| 5,660,854 A | 8/1997 | Haynes et al. | |
| 5,741,551 A | 4/1998 | Guire et al. | |
| 5,879,713 A | 3/1999 | Roth et al. | |
| 5,900,481 A | 5/1999 | Lough et al. | |
| 5,972,366 A | 10/1999 | Haynes et al. | |
| 6,133,436 A | 10/2000 | Köster et al. | |
| 6,143,037 A | 11/2000 | Goldstein et al. | |
| 6,228,393 B1 | 5/2001 | DiCosmo et al. | |
| 6,254,854 B1 | 7/2001 | Edwards et al. | |
| 6,261,537 B1 | 7/2001 | Klaveness et al. | |
| 6,287,204 B1 | 9/2001 | Kobayashi | |
| 6,287,285 B1 | 9/2001 | Michal et al. | |
| 6,287,604 B1 | 9/2001 | Sokoll et al. | |
| 6,306,422 B1 | 10/2001 | Batich et al. | |
| 6,444,318 B1 * | 9/2002 | Guire et al. | 428/412 |
| 6,461,631 B1 * | 10/2002 | Dunn et al. | 424/426 |
| 6,497,729 B1 | 12/2002 | Moussy et al. | |
| 6,503,556 B2 | 1/2003 | Harish et al. | |
| 6,669,980 B2 | 12/2003 | Hansen | |
| 6,673,385 B1 | 1/2004 | Ding et al. | |
| 6,689,473 B2 * | 2/2004 | Guire et al. | 428/412 |
| 7,144,573 B2 * | 12/2006 | Guire et al. | 424/78.08 |
| 7,195,913 B2 * | 3/2007 | Guire et al. | 435/401 |
| 7,361,724 B2 * | 4/2008 | Guire et al. | 528/196 |
| 2001/0013166 A1 | 8/2001 | Yan | |
| 2002/0013298 A1 | 1/2002 | Hunter | |
| 2002/0041899 A1 | 4/2002 | Chudzik et al. | |
| 2003/0064965 A1 | 4/2003 | Richter | |
| 2005/0147690 A1 | 7/2005 | Masters et al. | |

FOREIGN PATENT DOCUMENTS

| | | |
|---|---|---|
| EP | 0 449 592 | 10/1991 |
| EP | 0 455 905 | 11/1991 |
| JP | 5-123394 | 5/1993 |
| JP | 10-234846 | 9/1998 |
| JP | 11-89930 | 4/1999 |
| WO | 93/06925 | 4/1993 |
| WO | 95/20381 | 8/1995 |
| WO | 98/56353 | 12/1998 |

(Continued)

OTHER PUBLICATIONS

PCT Search Report for International Application No. PCT/US 02/31085 mailed on Oct. 5, 2001.

Wichert, et al., (1993) *Low molecular weight PLA: a suitable polymer for pulmonary administered microparticles*? J. Microencapsulation, vol. 10, No. 2: 195-207.

Chmura, et al., (2001) *Antibodies with infinite affinity*, Proc. Nat'l. Acad. Sci., vol. 98, No. 15: 8480-8484.

Arshady (1991) *Beaded polymer supports and gels, I. Manufacturing techniques*, Journal of Chromatography, vol. 586: 181-197.

(Continued)

*Primary Examiner* — D L Jones

(74) *Attorney, Agent, or Firm* — Kagan Binder, PLLC

(57) ABSTRACT

Surface coatings including microparticles immobilized in a matrix of polymeric material on a substrate are described. The microparticles can also include an agent which can be useful for various applications, such as medical applications.

This invention relates to the field of surface coatings for use in various applications. More particularly, the invention relates to surface coating useful for drug delivery, imaging and other uses of microparticles immobilized via a polymeric matrix.

16 Claims, 5 Drawing Sheets

(56) References Cited

FOREIGN PATENT DOCUMENTS

| | | |
|---|---|---|
| WO | 98/58990 | 12/1998 |
| WO | 99/47176 | 9/1999 |
| WO | 99/47253 | 9/1999 |
| WO | 00/39587 | 7/2000 |
| WO | 00/40593 | 7/2000 |
| WO | 00/51136 | 8/2000 |
| WO | 01/58384 | 8/2001 |
| WO | 01/59432 | 8/2001 |
| WO | 01/87267 | 11/2001 |
| WO | 01/89595 | 11/2001 |
| WO | 02/00162 | 1/2002 |
| WO | 02/36126 | 5/2002 |
| WO | 02/43788 | 6/2002 |
| WO | 02/071955 | 9/2002 |

OTHER PUBLICATIONS

Arshady, (1991) *Beaded polymer supports and gels, II. Physicochemical criteria and functionaliziation*, Journal of Chromatography, vol. 586: 199-219.

Mescher, (1992) *Surface Contact Requirements for Activation of Cytotoxic T Lymphocytes*, Journal of Immunology, vol. 149: 2402-2405.

Mayer, et al., (1994) *Biodegradable Materials: Balancing Degradability and Performance*, Trends in Polymer Science, vol. 2, No. 7: 227-235.

Jagur-Grodzinski, (1999) *Biomedical application of functional polymers*, Reactive & Functional Polymers, vol. 39: 99-138.

Hayashi, et al., (1993) *Immobilization of Thiol Proteases onto Porous Poly(vinyl alcohol)Beads*, Polymer Journal, vol. 25, No. 5: 489-497.

Notice of Reasons for Rejection, JP Application No. 2011-024327, mailed Jan. 29, 2013, with English Translation 0.

\* cited by examiner

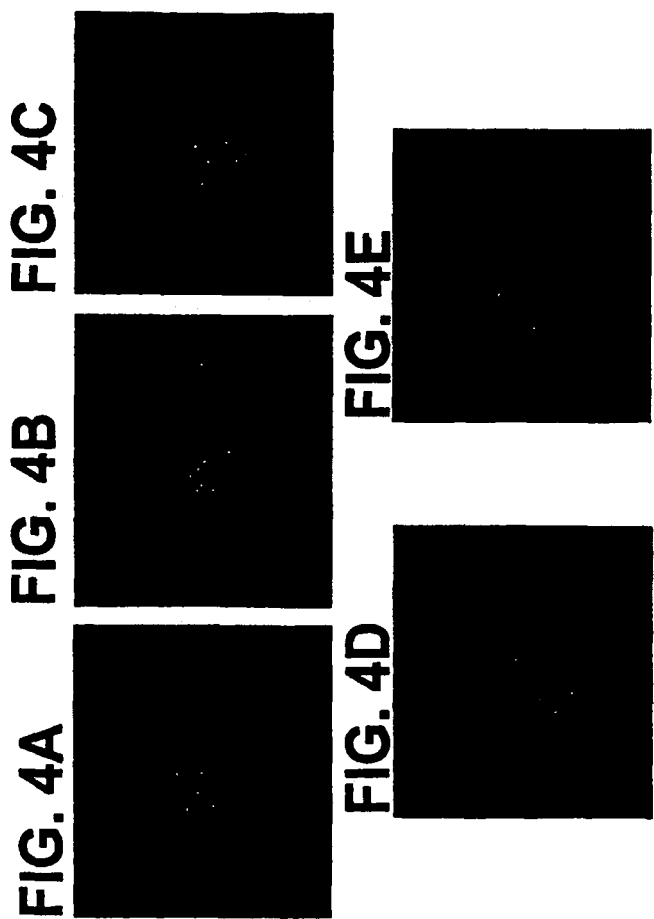

PARTICLE IMMOBILIZED COATINGS AND USES THEREOF

CROSS-REFERENCE TO RELATED APPLICATIONS

The present application claims the benefit of and is a continuation of commonly-owned U.S. Nonprovisional patent application Ser. No. 10/261,110, filed Sep. 30, 2002, now U.S. Pat. No. 8,158,106 titled PARTICLE IMMOBILIZED COATINGS AND USES THEREOF, which claims the benefit of U.S. Provisional Patent Application No. 60/327,441, filed Oct. 5, 2001, titled PARTICLE IMMOBILIZED COATINGS AND USES THEREOF, both of which are fully incorporated herein by reference.

FIELD OF THE INVENTION

This invention relates to the field of surface coatings for use in various applications. More particularly, the invention relates to surface coatings useful for drug delivery, device imaging and utilizing microparticles immobilized via a polymeric matrix.

BACKGROUND OF THE INVENTION

Functionalization of the surfaces of biomaterials and medically implantable devices has become increasingly common as it can lend to compatibility with a host system or can provide various advantages within the host system. Common functionalized materials include metals, ceramics, polymers, and glasses that can be used in a wide variety of medical applications. Modification of the substrate surface can include changes to the physical topography of the surface, for example, changes to the three dimensional characteristics of the surface; changes to biochemical properties of the surface (for example, to aid in drug delivery); or changes in the mechanical and optical properties of the surface.

Advances in life sciences has led to an increased demand for novel and improved technologies in surface coatings.

SUMMARY OF THE INVENTION

The current invention generally relates to substrates coated with microparticles, methods for coating such substrates, and uses for microparticle-coated surfaces. More specifically, the invention describes methods for coating substrates with a mixture of a polymeric material and microparticles, wherein the mixture is disposed on a surface of the substrate and the microparticles are immobilized in a matrix formed by the polymeric material.

In one embodiment the invention provides a surface, such as a surface of a substrate or a device, having a matrix that includes polymeric material and at least one reactive group. The matrix is covalently attached to the surface by the reactive group. The polymeric material can be polymers, copolymers, or combinations thereof. Within the matrix are immobilized a plurality of microparticles. The microparticles are generally immobilized in the matrix formed by the polymeric material. In one embodiment, the reactive groups are photoreactive groups. In another embodiment the matrix also includes a polymer crosslinking compound.

In some cases, the microparticles are immobilized in the matrix of polymeric material by entrapment and the entrapment of the microparticles does not depend on the formation of ionic or covalent bonds between the microparticles and the polymeric material. In some embodiments the microparticles are coupled to a functional agent, thereby providing the substrate with a desirable property afforded by the functional agent. In some cases the functional agent is a biologically active agent. Also, the microparticles can be of a biologically active material and, in some cases, are degradable.

In one embodiment the invention provides a kit for coating a substrate that includes at least one set of microparticles and a matrix-forming material. The matrix forming material includes polymeric material and one or more reactive groups. The matrix-forming material is configured and arranged to be covalently attached to the surface of a substrate via the one or more reactive groups and able to immobilize the microparticles on the surface of the substrate. The kit also provides instructions for preparing a coated surface.

In one embodiment, the substrate comprises a medical device and the microparticles immobilized on the medical device are coupled to, or have incorporated, a biologically active agent. In another embodiment, the microparticles coated on the medical device are detectable using imaging instrumentation. Microparticles having paramagnetic material, vapor phase material, or radioisotopic material can be coated on the surface of a medical device and be detected by the appropriate imaging instrumentation.

In another embodiment, the invention provides a method for coating a surface with a polymeric material and microparticles. A mixture of a polymeric material, a reactive group, and microparticles are prepared, disposed on a surface of a substrate, and then treated to attach the polymer to the surface of the substrate and immobilize the microparticles. In one embodiment, the polymer includes photoreactive groups and the mixture is treated with electromagnetic energy, thereby attaching the polymer to the substrate and crosslinking the polymer to immobilize the microspheres.

In another embodiment the invention provides a method for administering at least one biologically active agent to a subject. This is accomplished by providing a device that has a matrix covalently attached to the surface of the device. The matrix includes a polymeric material and at least one reactive group and the matrix is covalently attached to the surface by the reactive group. The polymeric material comprises a polymer, copolymer, or combinations thereof. A plurality of microparticles that includes at least one biologically active agent is immobilized in the matrix. The biologically active agent becomes available to the subject by placing the device in a subject or delivering the device to a subject.

In some embodiments the plurality of microspheres includes two or more sets of microspheres. In some cases a first functional agent and a second functional agent, which are otherwise mutually incompatible in a certain environment, are delivered from a first set of microparticles and a second set of microparticles that are immobilized in the polymer matrix.

In other embodiments, a first functional agent and second functional agent are released at different rates from a first set of microparticles and a second set of microparticles, respectively.

In another embodiment, a method for detecting a device is provided. The method involves taking a device having a matrix of polymeric material and microparticles immobilized in the matrix. The microparticles are detectable by magnetic resonance, ultrasonic imaging, radioisotopic imaging, or photonic imaging. The device is placed in a subject or an object and detected using appropriate imaging instrumentation. In some embodiments the device is a medical device and the subject is a patient.

In another embodiment, a cell-reactive surface is provided. The cell-reactive surface includes a surface having a matrix of polymeric material having immobilized microparticles arranged to provide a topography for cell interaction. In some cases, the surface can promote or inhibit the attachment of cells and also allow for cell adhesion and growth. In some embodiments, the microparticles are coupled to a molecule that is reactive with cell surface proteins.

BRIEF DESCRIPTION OF THE DRAWINGS

FIGS. 4a-4e are photomicrographs of microparticles immobilized within a polymeric matrix on a substrate.

DETAILED DESCRIPTION OF THE INVENTION

Figure 1:
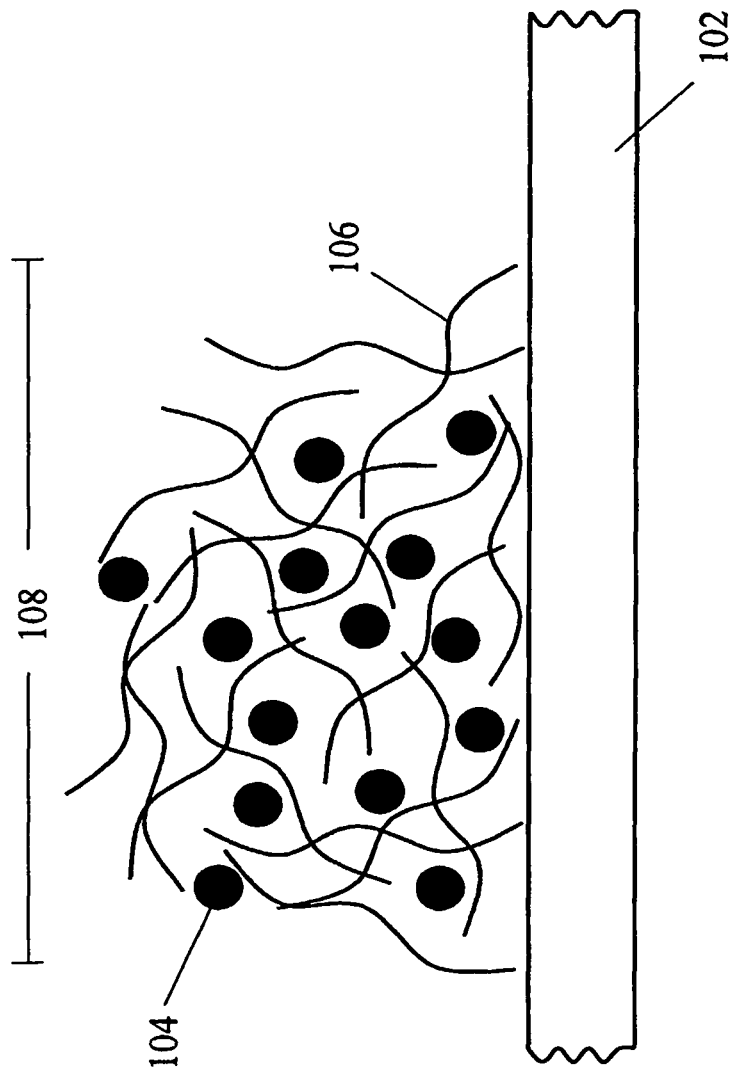
FIG. 1 is an illustration of a coating of microparticles in a polymeric matrix immobilized on a substrate.

In one aspect of the invention, a mixture is prepared that includes microparticles and polymeric material and the mixture is disposed on a substrate and treated to provide the substrate with a coating of microparticles immobilized in a matrix of polymeric material. As used herein, "polymer" and "polymeric material" refers to polymers, copolymers, and combinations thereof that can be used to form the matrix. The coating of microparticles can provide desirable properties to the surface of the substrate. Generally, the term "solid support" or "substrate" refers to a material on which can be coated a mixture of microparticles and polymeric material. Typically, the substrate is a device, such as a medical device, and the coating of microparticles in a polymeric matrix imparts a desirable property to the device. In some embodiments the microparticles are coupled to or associated with one or more functional agents. As used herein, "functional agent" refers to a compound or composition that provides the device with a useful property, such as a biologically, chemically, or physically useful property.

In one aspect, the present invention is particularly advantageous in that it provides a simple and efficient method for preparing surfaces that have diverse properties. For example, the methods described herein provide for preparation of surfaces that can have both biologically useful and detectable properties. In another example, the methods described herein provide for the preparation of surfaces that can deliver pharmaceutical compounds that are not typically compatible in one solvent.

The invention is also advantageous in that it provides a fast and accurate method for preparing surfaces having a precise amount of drug or pharmaceutical agent. Microparticles having a defined amount of a drug or pharmaceutical agent can be included in microparticles, for example, degradable microparticles, and can be coated onto a device in a polymeric matrix to provide the surface of the device with a precise amount of a drug or pharmaceutical agent contained within microparticles.

In preferred embodiments, the mixture containing a polymeric material and microparticles is directly disposed on a surface of a substrate and then treated to form a polymeric matrix to immobilize the microparticles in the matrix on the surface. In other embodiments, the polymeric material is disposed on a substrate and treated; microparticles are subsequently disposed on the treated material and immobilized on the substrate.

Substrate

The composition of the substrate can include biological or nonbiological, organic or inorganic materials. Suitable substrates include, but are not limited to, functionalized and non-functionalized substrates made of plastics, ceramic, resins, polysaccharides, silicon, or silica-based materials, glass, metals, films, gels, membranes, nylon, natural fibers such as silk, wool and cotton and polymers. The surfaces of substrates such as glass slides or silicon chips can also be modified, for example, by silanization, which can be useful for the immobilization of microparticles. Useful substrates also include cell culture plates, adherent and non-adherent surfaces, tissue engineering scaffolds, and cell columns. The substrate can also be of any dimension or size.

In some embodiments, the substrate is a portion of a medical device. In these embodiments, the surface of the medical device is typically coated with a mixture containing microparticles and a polymeric matrix. Medical devices that can be used as substrates include, but are not limited to, implantable medical devices, non-implantable medical devices, and surgical instruments. Non-limiting examples include stents, catheters, pacemakers, breast implants, venous or arterial clips, pins, braces, dental composites, heart valves, artificial hearts, defibrillators, prosthetics, artificial joints, auditory implants, neural stimulators, embolization devices, occlusion devices, ablation devices, biopsy devices, pumps, including infusion pumps, balloons, sealants, contact lenses, hemostats, needles, blades, saws, and monitors, such as oxygen or glucose monitors.

In another embodiment the substrate can be a portion of an optical device. Optical devices that can be used as substrates include, but are not limited to, for example, fiber optic cables, particularly ends of fiber optic cables, light emitting diodes, lenses, optical discs, for example, recordable and non-recordable compact discs and digital video discs, wave guides, reflectors, gratings, interference mirrors, and the like.

In another embodiment, the substrate can be a portion of a device used in food preparation, or in sanitary processes. However, other devices or substrates, wherein a coating of microparticles can impart a desirable property are also included in this invention.

In one embodiment the substrate is coated with a mixture of polymeric material and microparticles to provide a cell-reactive surface. As used herein "cell-reactive" refers to the ability of coated substrate to have an effect on cells, tissue, and other biological material that can be in contact with the coated substrate. Cells, tissue, other biological material include eukaryotic cells, prokaryotic cells, viruses, other biological particles, and any sort of biological material the cells or particles may produce, for example extracellular material. The coated surface can be prepared to promote or inhibit the attachment of cells to the surface, or can be used to provoke a cellular response by passive interaction of the cell with the coated surface. The coated substrate can be used in vivo or in vitro to provide various useful devices such as cell culture plates, tissue engineering scaffolds, cell columns, or any nucleus for the development of tissues in vivo, such as artificial lymph nodes. The cell-reactive surface can be provided by the surface topography of the surface coated with the polymeric material and microparticles. For example, microparticles of an appropriate size can be used to either promote or inhibit the interaction of cells as it has been shown that size of microspheres contributes to the interaction of certain cell types (Mescher, M. F. (1992) J Immunol, 149:2402). Microparticles can also be coupled to various moieties that are reactive with cell surface proteins and that can induce cellular responses.

In some cases, the substrate is pre-coated with a compound that can facilitate the immobilization of microparticles in a polymeric matrix. The substrate can be cleaned, pretreated or cleaned and pretreated prior to attachment of the microparticles. In one example, the substrate is silane treated by dipping it in a mixture of 1% p-tolydimethylchlorosilane (T-silane) and 1% N-decyldimethylchlorosilane (D-silane, United Chemical Technologies, Bristol, Pa.) in acetone, for 1 minute. After air drying, the substrate is cured in an oven at 120° C. for one hour. The substrate is then washed with acetone followed by dipping in distilled water. The substrate is further dried in an oven for 5-10 minutes. In some applications, other silanizing reagents, for example, hydrosiloxane derivatives, can be used to pretreat the substrate. The substrate can also be coated with an organosilane material and can be, for example, organosilane coated glass or ceramic. Other pretreatment or washing steps will be apparent upon review of this disclosure.

Microparticles

The microparticles of the invention can comprise any three-dimensional structure that can be immobilized on a substrate within a polymeric matrix. In some embodiments the microparticle can also be associated with at least one agent. In these embodiments, the agent or agents associated with the microparticle can impart a desirable property to the surface of the substrate.

According to the invention, the microparticle can be fabricated from any insoluble or solid material. Suitable materials include, for example, synthetic polymers such as poly(methylmethacrylate), polystyrene, polyethylene, polypropylene, polyamide, polyester, polyinylidenedifluoride (PVDF), and the like; degradable polymers such as poly(lactide-co-glycolide) (PLGA) and chitosan (poly-[1→4]-β-D-glucosamine), and the like; glass, including controlled pore glass (CPG) and silica (nonporous glass); metals such as gold, steel, silver, aluminum, silicon, copper, ferric oxide, and the like; natural polymers including cellulose, crosslinked agarose, dextran, and collagen; magnetite, and the like. Examples of useful microparticles are described, for example, in "Microparticle Detection Guide" from Bangs Laboratories, Fishers, Ind. Optionally, microparticles can be obtained commercially, from, for example, Bangs Laboratories (Fishers, Ind.), Polysciences (Germany), Molecular Probes (Eugene, Oreg.), Duke Scientific Corporation (Palo Alto, Calif.), Seradyn Particle Technology (Indianapolis, Ind.), and Dynal Biotech (Oslo, Norway).

In some embodiments, the microparticles are not modified prior to preparation of the microparticle-containing mixture and disposing of the microparticles on the substrate. In these embodiments, the microparticle itself can provide a desirable or useful property when immobilized in a polymeric matrix on a substrate. For example, paramagnetic microparticles composed of, for example, iron oxide, can provide the surface of a substrate with paramagnetic properties; silica can provide the surface of a substrate with refractive properties; and metallic microparticles can provide the surface of a substrate with reflective properties. In yet another example, microparticles of a suitable size can provide a surface of a substrate that is suitable for interactions with various cell types.

The microparticles can be of any size, but preferably the microparticle is in the range of 5 nm to 100 μm in diameter, more preferably in the range of 100 nm to 20 μm in diameter, and even more preferably in the range of 400 nm to 20 μm in diameter.

In one preferred embodiment, degradable microparticles are utilized for surface coatings. Degradable microparticles can include, for example, dextran, poly-lactic acid, poly(lactide-co-glycolide), polycaprolactone, polyphosphazine, polymethylidenemalonate, polyorthoesters, polyhydroxybutyrate, polyalkeneanhydrides, polypeptides, polyanhydrides, polyesters, and the like. Degradable polymers useful for the current invention can be obtained from, for example, Birmingham Polymers, Inc. (Birmingham, Ala. 35211). Degradable polymers and their synthesis have been also been described in various references including Mayer, J. M., and Kaplan, D. L. ((1994) *Trends in Polymer Science* 2: pages 227-235; and Jagur-Grodzinski, J., (1999) *Reactive and Functional Polymers: Biomedical Application of Functional Polymers*, Vol. 39, pages 99-138. In some cases, the degradable microparticle is a biodegradable microparticle that can be degraded in vivo. For example, the biodegradable microparticles can be degraded by the action of various enzymes in the body.

In some cases the degradable microparticle can be a mixture of a degradable material and a plastic. The degradable is also preferably nontoxic although in some cases the microparticles can include an agent which is useful for the selective prevention of prokaryotic or eukaryotic cell growth, or elimination of cells, such as chemotherapeutic agents or antimicrobials. Degradable microparticles can include biologically active agents that can be released from the surface of the coated substrates upon degradation of the microparticle.

In one embodiment, the degradable microparticle contains a biologically active agent, for example a pharmaceutical or a prodrug. Degradable microparticles can be prepared incorporating various biologically active agents by established techniques, for example, the solvent evaporation technique (see, for example, Wichert, B. and Rohdewald, P. *J Microencapsul*. (1993) 10:195). The biologically active agent can be released from the microparticle, which is immobilized in the polymeric matrix on a substrate, upon degradation of the microparticle in vivo. Microparticles having biologically active agent can be formulated to release a desired amount of the agent over a predetermined period of time. It is understood that factors affecting the release of the agent and the amount released can be altered by the size of the microparticle, the amount of agent incorporated into the microparticle, the type of degradable material used in fabricating the microparticle, the amount of microparticles immobilized per unit area on the substrate, etc.

In one embodiment, the invention advantageously allows for preparation of surfaces having two, or more than two, different functional agents, wherein the functional agents are mutually incompatible in a particular environment, for example, as hydrophobic and hydrophilic drugs are incompatible in either a polar or non-polar solvent. Different functional agents may also demonstrate incompatibility based on protic/aprotic solvents or ionic/non-ionic solvents. For example, the invention allows for the preparation of one set of degradable microparticles containing a hydrophobic drug and the preparation of another set of degradable microparticles containing a hydrophilic drug; the mixing of the two different sets of microparticles into a polymeric material used to form the matrix; and the disposing of the mixture on the surface of a substrate. Both hydrophobic and hydrophilic drugs can be released from the surface of the coated substrate at the same time, or the composition of the degradable microparticles or polymeric matrix can be altered so that one drug is released at a different rate or time than the other one.

In some cases it can be advantageous to prepare degradable microparticles having a composition that is more suitable for either hydrophobic or hydrophilic drugs. For example, useful degradable polymers or degradable copolymers for hydrophobic drugs have a high lactide or high caprolactone content;

whereas useful degradable polymers or degradable copolymers for hydrophilic drugs have a high glycolide content.

Traditional coating procedures directed at disposing at least two different types of functional agents have often required that the functional agents be put down separately. For example, solubilizing a hydrophobic drug in a non-polar solvent, coating the surface of the substrate with the non-polar mixture, drying the non-polar mixture, solubilizing the hydrophilic drug in a polar solvent, coating the layer of the dried non-polar mixture with the polar mixture, and then drying the polar mixture. This process can be inefficient and can also result in undesirable surface properties (e.g., the layering of the drugs will cause one drug to be released before the other one is released). According to the invention, the method of preparing surfaces having two, or more than two, different functional agents, in particular when the two different functional agents are released from the surface of the substrate, is a significant improvement over traditional methods of coating substrates and delivering functional agents from the surface of the substrates.

Other types of non-degradable microparticles can also be useful for the release of a functional agent from the surface of a coated device. Such non-degradable microparticles include pores and can be silica microparticles, for example. Porous non-degradable microparticles can also be used for incorporation of an agent, such as a biologically active agent. Microparticles having particular pore sizes can be chosen based on the type and size of the agent to be incorporated into the pores. Generally, the microparticle having pores can be soaked in a solution containing the desired agent wherein the agent diffuses into the pores of the microparticle. Substrates can be prepared having a coating of these microspheres in a polymeric matrix. Upon placing the coated substrate in fluid-containing environment, for example in a subject, the agent can be released from the microspheres and be delivered to the subject.

The type of polymer, as well as the concentration of the polymer and the extent of polymer crosslinking in the polymeric matrix, can have an affect on the delivery of the biologically active agent from the surface of the coated device. For example, polymeric matrix material having charged portions may either decrease or increase the rate of release of a charged biologically active agent from the surface of the coated device, depending on whether there are attractive or repulsive forces between the two. Similarly, hydrophilic and hydrophobic polymeric matrix material can also have an affect on the rate of release of hydrophilic and hydrophobic biologically active agents, in particular hydrophilic and hydrophobic drugs. In polymeric matrices having a high concentration of polymer or in matrices wherein the polymer is highly crosslinked, the rate of delivery of the drug can be decreased.

Microparticles can also have an outer coating to control the availability of the agent or agents that are associated with the microparticle. For example, microparticles can include an outer coating of poly(ethylene glycol) (PEG) which can provide sustained or controlled availability of the functional agent that is associated with the microparticle. This can be particularly useful on medical device surfaces that are coated, specifically implantable medical devices. Another useful outer coating can include, for example, a silane or polysiloxane coating.

In some applications, swellable microparticles can be employed for incorporation of; the functional agent. Such swellable microparticles are typically composed of polystyrene, copolymers of polystyrene and are typically swellable in an organic solvent. Microparticles can be soaked in organic solvents containing the functional agent in order for the agent to be incorporated into the microparticle. The solvent swells the polymeric microparticles and allows the functional agent to penetrate into the microparticles' cores. Excess solvent is then removed, for example, by vacuum filtration, entrapping the functional agent in the hydrophobic interior regions of the microparticles. In one such embodiment, poly(methylsytrene)-divinyl benzene microparticles are rinsed in dimethylformamide. A solution containing the functional agent in dimethylformamide is then added to the microparticles, and the microparticles and solution are incubated with agitation overnight. Excess functional agent is removed from the suspension by vacuum filtration using membrane filters, such as those provided by Millipore Company (Bedford, Mass.). The filtered microparticles are then sonicated and washed by centrifugation in distilled water containing 0.01% Tween 20 to remove residual functional agent on the outside of the microparticles.

In some embodiments it is preferable that the swellable microparticle is impregnated with a functional agent that is detectable using common imaging techniques, for example a paramagnetic material, such as nanoparticular iron oxide, Gd, or Mn, or a radioisotope. This can be useful for detection of medical devices that are implanted in the body or that travel through a portion of the body. Such coated medical devices can be detected by paramagnetic resonance imaging, ultrasonic imaging, or other suitable detection techniques. In another example, microparticles that contain a vapor phase chemical can be used for ultrasonic imaging. Useful vapor phase chemicals include perfluorohalocarbons, such as perfluoropentane and perfluorohexane, which are described in U.S. Pat. No. 5,558,854 (Issued 24 Sep., 1996); other vapor phase chemicals useful for ultrasonic imaging can be found in U.S. Pat. No. 6,261,537 (Issued 17 Jul., 2001); the teaching of these patents are incorporated by reference.

The microparticles of the invention can possess one or more desirable properties, such as ease of handling, dimensional stability, optical properties, sufficient size and porosity to adequately couple the desired amount of agent or agents to a substrate, and the like. The microparticles can be chosen to provide additional desired attributes, such as a satisfactory density, for example, a density greater than water or other solvent used in application of the microparticles to the substrate.

Coupler

In one embodiment, the microspheres include a "coupler" that can allow the coupling of a functional agent to the microparticle. As used herein, "coupler", "coupling compound", or "coupling moiety" refers to any sort of entity that allows a functional agent to be attached to the microparticle. The coupler can have one member or more than one member. For example, the coupler can be a small molecule, or, can be a binding pair that consists of more than one larger molecule, for example a pair of interacting proteins.

The microparticles can be prepared to include a coupler having reactive groups. The coupler having reactive groups can be used for coupling one or more functional agents to the microparticle, for example, biologically active agents or functional agents conferring optical properties. In other embodiments, reactive groups provided on the microparticle can be used for coupling the microparticle to the polymeric material or for coupling the microparticle to the surface of the substrate, or any combination of the above. Suitable reactive groups can be chosen according to the nature of the functional agent that is to be coupled to the microparticle. Examples of suitable reactive groups include, but are not limited to, carboxylic acids, sulfonic acids, phosphoric acids, phosphonic acids, aldehyde groups, amine groups, thiol groups, thiol-reactive groups, epoxide groups, and the like. For example, carboxylate-modified microparticles can be used for covalent coupling of proteins and other amine-containing molecules using water-soluble carbodiimide reagents. Aldehyde-modified microparticles can be used to couple the microparticles to proteins and other amines under mild conditions. Amine-modified microparticles can be used to couple the microparticle to a variety of amine-reactive moieties, such as succinimidyl esters and isothiocyanates of haptens and drugs, or carboxylic acids of proteins. In another application, sulfate-modified microparticles can be used when the user desires to passively absorb a protein such as bovine serum albumin (BSA), IgG, avidin, streptavidin, and the like.

In another embodiment, the reactive groups can include such binding groups as biotin, avidin, streptavidin, protein A, and the like. These and other modified microparticles are commercially available from a number of commercial sources, including Molecular Probes, Inc. (Eugene, Oreg.).

Another method for coupling moieties of the invention is through a combination of chemical and affinity interactions, herein referred to as "chemi-affinity" interactions, as described by Chumura et al. (2001, Proc. Natl. Acad. Sci., 98:8480). Binding pairs can be engineered that have high binding specificity and a negligible dissociation constant by functionalizing each member of the binding pair, near the affinity binding sites of the pair, with groups that will react to form a covalent bond. For example, the constituents of each functionalized member can react, for example by Michael addition or nucleophilic substitution, to form a covalent bond, for example a thioether bond.

The surface of the microparticle can also be coated with crosslinking compounds. Various functional agents can be coupled to the microparticle via crosslinking agents. Commercially available crosslinking agents obtained from, for example, Pierce Chemical Company (Rockford, Ill.) can be used to couple the microparticles to functional agents via, for example, amine groups, provided on the surface of the microparticles. Useful crosslinking compounds include homobifunctional and heterobifunctional crosslinkers. Two examples of crosslinking compounds that can be used on microparticles presenting, for example, amine groups, are di-succinimidyl suberate and 1,4-bis-maleimidobutane.

Functional Agent

In some embodiments the microparticles are be coupled to, or associated with, a functional agent. As used herein, "functional agent" typically refers to one or more compounds that can be coupled to, or associated with, the microparticles and can provide the surface of the coated substrate with a property that is conferred by that compound. Useful functional agents include biologically active compounds, compounds with detectable properties, such as paramagnetic compounds, and compounds with optical properties. The microparticles of the invention can be coupled to, or associated with, any physiologically active substance that produces a local or systemic effect.

In one embodiment, the microparticles are coupled to a biologically active compound, for example, a pharmaceutical or other compound that can be used to treat a medically condition. One group of particularly useful biologically active compounds are "hemo-active" compounds. As used herein, "hemo-active" refer to compounds that can affect hemostasis in the body, that is, events involved in blood clotting/coagulation and blood clot dissolution processes. These events include, but are not limited to vascular constriction, platelet activation, platelet clumping, activation clotting factors, and dissolution of fibrin clots. Useful hemo-active agents include thrombolytic factors, for example, plasminogen activator (TPA) and streptokinase; clotting cascade factors, for example, protein S; anti-coagulant compounds, for example, heparin and nadroparin (low molecular weight heparin), and warfarin, anti-platelet, for example, ticlopidine, and the like.

Another group of useful biologically active compounds are antibiotics. Examples of antibiotics include penicillin, tetracycline, chloramphenicol, minocycline, doxycycline, vancomycin, bacitracin, kanamycin, neomycin, gentamycin, erythromycin and cephalosporins. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone.

Another group of useful biologically active compounds are antiseptics. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Another group of useful biologically active compounds are anti-viral agents. Examples of anti-viral agents include α-methyl-P-adamantane methylamine, [hydroxy-ethoxy]methylguanine, adamantanamine, 5-iodo-2'-deoxyuridine, trifluorothymidine, interferon, and adenine arabinoside.

Another group of useful biologically active compounds are enzyme inhibitors. Examples of enzyme inhibitors include edrophonium chloride, N-methylphysostigmine, neostigmine bromide, physostigmine sulfate, tacrine HCl, tacrine, 1-hydroxy maleate, iodotubercidin, p-bromotetramisole, 10-(α-diethylaminopropionyl)-phenothiazine hydrochloride, calmidazolium chloride, hemicholinium-3,3,5-dinitrocatechol, diacylglycerol kinase inhibitor 1, diacylglycerol kinase inhibitor II, 3-phenylpropargylaminie, N-monomethyl-L-arginine acetate, carbidopa, 3-hydroxybenzylhydrazine HCl, hydralazine HCl, clorgyline HCl, deprenyl HCl, L(−), deprenyl HCl, D(+), hydroxylamine HCl, iproniazid phosphate, 6MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthine, papaverine HCl, indomethacin, 2-cyclooctyl-2-hydroxyethylamine hydrochloride, 2,3-dichloro-α-methylbenzylamine (DCMB), 8,9-dichloro-2,3,4,5-tetrahydro-1H-2-benzazepine hydrochloride, p-aminoglutethimide, p-aminoglutethimide tartrate, R(+), p-aminoglutethimide tartrate, S(−), 3-iodotyrosine, alpha-methyltyrosine, L(−), alpha methyltyrosine, D L(−), cetazolamide, dichlorphenamide, 6-hydroxy-2-benzothiazolesulfonamide, and allopurinol.

Another group of useful biologically active compounds are anti-pyretics and antiinflammatory agents. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide. Local anesthetics are substances which have an anesthetic effect in a localized region. Examples of such anesthetics include procaine, lidocaine, tetracaine and dibucaine.

Other biologically active compounds or pharmaceuticals that can be used in the current invention include, but are not limited to, antiproliferative agents, for example, taxol, rapamycin, and vinorelbine, growth factors, for example, insulin-like growth factor (IGF-1) and transforming growth factor-beta 1 (TGF-beta1), and other agents, for example, antimicrobials, antiallergenics, antihistamines, analgesics, nutrients, vitamins, steroids, decongestants, miotics, sedatives, hypnotics, tranquilizers, estrogens, progestational agents, humoral agents, prostaglandins, antispasmodics, antimalarials, and antihypertensive agents. Also included are forms such as uncharged molecules, molecular complexes, salts, ethers, esters, amides, etc., which can be converted to an activated form when in a subject.

In addition, antigens or vaccines, for example, peptide antigens, can be coupled to or associated with the microparticles and can be used to illicit an immune response from the surface of the microparticles. For example, the unique peptides can be presented on a microparticle in a MHC tetrameric complex which can be used to promote a specific T cell response. A variety of other immune regulating compounds which are known in the art can be coupled to the microparticles to promote or quench an immune response.

The quantity of functional agents provided on each individual microparticle can be adjusted by the user to achieve the desired effect. Factors that can influence this can be, for example, on a medical device, the amount of anti-coagulant activity or, for example, on a cell culture device, the amount of cell adhesion factor or growth factor. The density of functional agents coupled to, or associated with, the microparticles can vary and can depend on, for example, the dose of a particular biologically active agent intended to be provided on the substrate. Biologically active compounds can be provided by the microparticles in a range suitable for the application. In another example, protein molecules can be provided by microparticles. For example, the amount of protein molecules present can be in the range of 1-250,000 molecules per 1 µm diameter microparticle. However, depending on microparticle source and preparation the amount of agent coupled to, or associated with, the microsphere can vary.

The quantity and organization of the microparticles themselves on a substrate can also impart desirable properties to the substrate, for example, on an optical or imaging device. For paramagnetic resonance or ultrasonic imaging applications, the number of microparticles immobilized on a device can be directly correlated with the imaging signal strength. To increase imaging signal strength, a high density of microparticles can be immobilized in a localized area on the device. Alternately, the density of microparticles over the device can vary, thereby allowing different regions of the device to be imaged distinctly. This can be accomplished by coating the different regions of the device with two or more different coating slurries with differing concentrations of microparticles. In optical applications, the organization of microparticles on the surface can provide the device with useful properties. A mixture of polymeric material and microparticles can be disposed and patterned on a surface by irradiating through a patterned mask to create a grating. The spacing of the grating can be determined by factors such as the dimensions of the mask and the dimensions of the microparticles on the substrate. Additionally, other optical devices can be created with a close packing of microparticles. Such devices can be created by allowing the microparticles in a concentrated mixture to assemble on a substrate prior to matrix formation. The packing and subsequent optical properties of such a coating will depend on the microparticle dimensions.

Coupling the functional agent to, or associating the functional agent with the microparticle prior to disposing of the microparticle can provide benefits in substrate coating. For example, as compared to directly coupling an agent to a substrate, a higher density of agent per surface area of substrate can be achieved by first coupling functional agent to the microparticle. Also, the coupling of an agent to the microparticle in solution is generally more efficient than the direct coupling of a functional agent to a substrate, resulting in a lower loss of functional agent during the coupling procedure. Additionally, coupling of a functional agent to a microparticle in solution generally allows for more variability during the coupling process. For example, coupling procedures that require agitation of the coupling solution, such as stirring, can readily be achieved using microparticles in the stirred solution. Additionally, determination of the amount of functional agent coupled per microparticle can readily be achieved by performing, for example, immunofluorescence flow cytometry or a protein assay, such as a BCA assay, on a portion of the microparticles following coupling to the functional agent. Once the microparticles have been coupled with the desired amount and type of functional agent, these functional agent-coupled microparticles can then be included in a mixture containing a suitable polymeric material or can be disposed on a substrate that has been coated with a polymeric material.

In some embodiments, the functional agent can be modified prior to coupling with the microparticle. In other words, a portion of the coupler can be attached to the functional agent prior to the functional agent being coupled to the microparticle. For example, the functional agent can be derivatized with one member of a binding pair, and the microparticles derivatized with the other member of the binding pair. Suitable binding pairs include avidin:biotin, streptavidin:biotin, antibody:hapten, for example anti-digoxigenin Ab:digoxigenin or anti-trinitrophenyl Ab:trinitrophenyl. For example, the functional agent can be biotinylated by, for example, cross-linking the biotin to the functional agent using methods known in the art. The biotinylated agent or agents can then be coupled with streptavidin provided on the surface of the microparticles. Members of the binding pair can be functionalized to provide chemi-affinity interactions as indicated above.

Matrix

According to the invention, the microparticles are immobilized on a substrate via a matrix that includes polymeric material. The matrix is generally a layer of polymeric material (herein also, a "layer") that has a thickness which is sufficient to immobilize the microparticles. As used herein, "immobilization" refers to the process wherein microparticles become positionally fixed within, or on, a matrix that has been formed on the surface of a substrate. As used herein, the terms "in a polymeric matrix" and "within a polymeric matrix" includes arrangements wherein microparticles are completely surrounded by the polymeric material and arrangements wherein microparticles that are partially surrounded by the polymeric material but that are held to the matrix primarily by non-chemical bonding interactions. It has been observed that some microparticles are stably associated with the matrix although the microparticles are not completely surrounded by polymeric material. Without intending to be bound by theory, it is thought that these microparticles become lodged in the pores of the matrix.

Immobilization of microparticles in a matrix on surface offers advantages over immobilizing particles on a surface by bonding, without the presence of a surrounding polymeric material. For example, sheer forces acting on a surface can break bonds between the microparticle and a surface, resulting in the loss of the particle from the surface. The presence of the matrix of polymeric material offers protection from these forces and therefore provides surface coatings having greater stability.

In a preferred embodiment, the microparticles are immobilized on the substrate by entrapment in a polymeric matrix. As used herein, "entrapment" refers to the positional fixation of microparticles within the polymeric matrix on the substrate where the positional fixation is due to the physical constraint of the microparticles by the network of polymeric strands and does not depend on covalent or ionic chemical bonding interactions between the microparticle and the substrate or between the microparticles and the polymer. An example of entrapped microparticles is shown in FIG. 1, wherein a polymeric material 106 is disposed on a substrate 102 and entraps the microparticles 104 within the polymeric material 106 thereby forming a coated substrate.

In another embodiment, the microparticles are immobilized by both a) physical constraints of the matrix of polymeric material on the microparticles (i.e., "entrapment") and b) any sort of chemical bonding (for example, ionic, covalent, coordinative, hydrogen or Van der Waals bonding, or combinations thereof) between the microparticles and portions of the matrix of polymeric material.

In one embodiment, immobilization is carried out by mixing microparticles with a polymeric material to create a mixture, disposing the mixture on a substrate, and then treating the mixture so the mixture forms a matrix wherein the microparticles become positionally fixed within or on the matrix.

In another embodiment, the polymeric material is first disposed on the substrate and treated. Subsequent to the treatment, microparticles are disposed on the treated material and immobilized on the matrix. This embodiment can be advantageous when, for example, the microparticles or an agent coupled to, or associated with, the microparticles is stable only in selected storage conditions.

The matrix can be composed of a variety of polymeric material that allows immobilization of the microparticles. As used herein, "polymer" and "polymeric material" refers to polymers, copolymers, and combinations thereof that can be used to form the matrix. The polymeric material used for formation of the matrix can be also be referred to as "matrix-forming material", or "matrix-forming polymeric material". In some cases the polymeric material is referred to as a "soluble polymer". Preferred materials for the matrix of polymeric material can be, but are not limited to, synthetic hydrophilic polymers which include polyacrylamide, polymethacrylamide, polyvinylpyrrolidone, polyacrylic acid, polyethylene glycol, polyvinyl alcohol, poly(HEMA), and the like; synthetic hydrophobic polymers such as polystyrene, polymethylmethacrylate (PMMA), polybutylmethacrylate (PBMA), polyurethanes, and the like; copolymers thereof, or any combination of polymers and copolymers. Natural polymers can also be used and include polysaccharides, for example, polydextrans, glycosaminoglycans, for example, hyaluronic acid, and polypeptides, for example, soluble proteins such as albumin and avidin, and combinations of these natural polymers. Combinations of natural and synthetic polymers can also be used.

In one preferred embodiment, the polymers and copolymers as described are derivitized with a reactive group, for example a thermally reactive group or a photoreactive group. The reactive groups can be present at the terminal portions (ends) of the polymeric strand or can be present along the length of the polymer. In one embodiment the photogroups are located randomly along the length of the polymer.

In some embodiments, polymer crosslinking compounds, for example photoreactive or thermally activated polymer crosslinkers, can be added to the polymeric material and can be treated to form the matrix. As used herein, "polymer crosslinking compound" refers to a compound that can be used to crosslink polymers, copolymers, or combinations thereof, together. The polymer crosslinking compound can include one or more reactive groups and these groups can be used to crosslink the polymer and can also be used to attach the polymer to the surface of the substrate. One example of a useful polymer crosslinking compound is bisacrylamide. In forming the matrix of polymeric material, a mixture including microparticles, the polymer, and a polymer crosslinking compound can be applied to the substrate and then treated to crosslink the polymers. The polymer can be crosslinked, for example, by activation of reactive groups provided by the polymer. Addition of polymer crosslinking compounds can serve to make the matrix of polymeric material more durable to use conditions and also can create matrices with smaller pore sizes capable of entrapping smaller microparticles.

In some embodiments the reactive groups provided on the polymer can be photoreactive groups and the photoreactive polymer can be crosslinked by irradiation. The microparticles become entrapped in the matrix of polymeric material which is formed by polymer crosslinking of the polymers. The photoactive groups can also serve to bind the polymer to the surface of the substrate upon activation of the photoreactive groups. The concentration of the polymer and the extent of crosslinking between the polymers can be adjusted according to the size or sizes of microparticles to be entrapped in the matrix of polymeric material.

According to this embodiment, photoreactive groups can be provided on a polymer. As used herein, a "photoreactive polymer" can include one or more "photoreactive groups." A "photoreactive group" includes one or more reactive moieties that respond to a specific applied external energy source, such as radiation, to undergo active species generation, for example, active species such as nitrenes, carbenes and excited ketone states, with resultant covalent bonding to an adjacent targeted chemical structure. Examples of such photoreactive groups are described in U.S. Pat. No. 5,002,582 (Guire et al., commonly owned by the assignee of the present invention), the disclosure of which is incorporated herein in its entirety. Photoreactive groups can be chosen to be responsive to various portions of the electromagnetic spectrum, typically ultraviolet, visible or infrared portions of the spectrum. "Irradiation" refers to the application of electromagnetic radiation to a surface.

Photoreactive aryl ketones are preferred photoreactive groups on the photoreactive polymer, and can be, for example, acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of preferred aryl ketones include heterocyclic derivatives of anthrone, including acridone, xanthone and thioxanthone, and their ring substituted derivatives. Particularly preferred are thioxanthone, and its derivatives, having excitation wavelengths greater than about 360 nm.

The azides are also a suitable class of photoreactive groups on the photoreactive polymer and include arylazides ($C_6R_5N_3$) such as phenyl azide and particularly 4-fluoro-3-nitrophenyl azide, acyl azides (—CO—$N_3$) such as ethyl azidoformate, phenyl azidoformate, sulfonyl azides (—$SO_2$—$N_3$) such as benzensulfonyl azide, and phosphoryl azides $(RO)_2PON_3$ such as diphenyl phosphoryl azide and diethyl phosphoryl azide.

Diazo compounds constitute another suitable class of photoreactive groups on the photoreactive polymers and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as 3-trifluoromethyl-3-phenyldiazirine, and ketenes (—CH=C=O) such as ketene and diphenylketene.

Exemplary photoreactive groups are shown as follows.

TABLE 1

| Photoreactive Group | Bond Formed |
|---|---|
| aryl azides | Amine |
| acyl azides | Amide |
| Azidoformates | Carbamate |
| sulfonyl azides | Sulfonamide |
| phosphoryl azides | Phosphoramide |
| Diazoalkanes | new C—C bond |
| Diazoketones | new C—C bond and ketone |
| Diazoacetates | new C—C bond and ester |
| beta-keto-alpha-diazoacetates | new C—C bond and beta-ketoester |
| aliphatic azo | new C—C bond |
| Diazirines | new C—C bond |
| Ketenes | new C—C bond |
| photoactivated ketones | new C—C bond and alcohol |

The photoreactive polymer can, in some embodiments, comprise a photoreactive copolymer. The polymer or copolymer can have, for example, a polyacrylamide backbone or be a polyethylene oxide-based polymer or copolymer. One example of a photoreactive polymer comprises a copolymer of vinylpyrrolidone and N-[3-(4-Benzoylbenzamido)propyl] methacrylamide (BBA-APMA); another example is a copolymer of acrylamide and BBA-APMA.

The photoreactive groups of the photoreactive polymer can allow the formation of a covalent bond between the substrate and the photoreactive polymer thereby binding the polymer to the surface of the substrate. The photoreactive groups of the photoreactive polymer can also serve to crosslink polymeric strands together, allowing the formation of a network of covalently crosslinked polymeric strands that serve as the matrix in which the microparticles can be entrapped. In some embodiments, a non-photoreactive crosslinking agent can be used to promote the formation of crosslinked polymeric strands. The use of a polymer crosslinking agent can depend, for example, on the location and number of photoreactive groups that are present on the polymeric strand. A polymer crosslinking agent can be added that can be a target for the photoreactive groups, that can initiate further polymerization of the polymers, or that can be thermochemically activated crosslinker, for example a DSS (N,N-disuccinimidyl suberate) crosslinker. The crosslinking agents can further solidify the matrix by bonding to other parts of the polymer.

The matrix can be formed from a variety of materials and preferably have pore sizes which allow the entrapment of the microparticle of the invention. For example, if entrapping microparticle with an average diameter of 2.5 µm, it is useful to have a pore size in the range of 50 nm to 2.5 µm, and more preferably in the range of 100 nm to 1 µm.

In a preferred embodiment, the matrix of polymeric material is permeable to various compounds, the compounds typically being smaller than smallest microparticle immobilized in the matrix. For example, in polymeric matrices that at least partially include a hydrophobic polymeric material, aqueous solutions which can include proteins and other molecules smaller than proteins can diffuse freely through the matrix.

In one preferred embodiment a matrix is formed from polymeric material sufficient to entrap the microparticles of the invention and also sufficient to allow the diffusion of molecules in and out of the matrix. In this embodiment, the matrix allows the immobilization of microparticles that are at least 100 nm diameter and allows the diffusion of molecules that are 50 nm or less, and more preferably, 25 nm or less, in and out of the matrix.

In another embodiment, immobilization of the microparticles can be performed by chemical bonding of the microparticle to the matrix and the matrix to the substrate. A variety of bonds can be formed between the microparticles and the matrix material, and the matrix material and the substrate. These bonds include, for example, ionic, covalent, coordinative, hydrogen and Van der Waals bonds. In this embodiment, covalent bonds are preferably formed.

In one embodiment, slurries including polymeric material and microparticles, which can be coupled to, or associated with, a functional agent, are dip-coated onto the surface of the substrate to form a coated surface. In another embodiment the polymeric material is dip-coated to form a coated surface. Alternatively, the polymeric material can be applied by jet printing to the surface of the substrate through utilization of a piezoelectric pump. Printing techniques can allow the application of a relatively small amount of the mixture at precise locations on the surface of the substrate. In another embodiment, the polymeric material is disposed on the substrate and treated; the microparticles are then placed and immobilized on the substrate via the treated material.

The mixture coating can be treated to cover a portion of the surface of the substrate. The coating of microparticles can be patterned at various locations on the surface of the substrate. The thickness of the matrix of polymeric material of each coated portion can vary and can depend on the size of the microparticles immobilized in the matrix. Preferably, the thickness of the matrix of polymeric material on the substrate is greater than the diameter of the largest microparticle being disposed on the substrate. In some applications, the substrate can be subject to more than one step of coating with a mixture of polymeric material and microparticles and treating, thereby allowing the formation of multiple layers on the substrate surface.

In order to create a surface coating of immobilized microparticles in a matrix, the mixture, which includes the polymeric material, is typically treated after the mixture is disposed on the substrate. In one embodiment, the polymeric material, which includes a photopolymer, is treated with electromagnetic energy, for example, with UV light, to activate the photoreactive groups of the polymer and to bind the polymer to the substrate or to bind the polymer strands together via crosslinking, or both. In some applications the polymeric material is treated with electromagnetic energy with a mask to form a pattern of treated material on the substrate.

In one embodiment, the microparticles are coupled to, or associated with, a biologically active agent and immobilized via a matrix of polymeric material on the surface of a substrate. In some cases, this coating technology is useful for providing a desired amount of a biologically active agent to the surface of a substrate, for example, the surface of a medically implantable device or a surgical instrument. Examples of such devices or instruments have been described above.

Examples of the usefulness of a device coated with microspheres including a biologically active agent are described below.

Uses for Coated Substrates

Heparin is frequently used for its anticoagulant characteristics in situations where foreign material introduced into the patient's body may be a site for the development of blood clots. The development of blood clots can not only produce obstruction of vessels but also can provide a source for emboli which can produce blood vessel obstruction at distant sites. Microparticles coupled to heparin and immobilized via a matrix of polymeric material can prevent clot formation on a surface normally predisposed to coagulation.

In one example, heart valves can be coated with a mixture containing a polymeric material and microparticles coupled to heparin or other anti-coagulant or throbolytic compounds. This anti-coagulant or throbolytic coating is useful since the surface of the valve is a frequent source of thrombosis and consequent emboli. There are also various uses for intravascular catheters in diagnostic and therapeutic cardiovascular disease. These catheters can also be coated with a mixture of polymeric material and microparticles coupled to, or associated with, a biologically active compound. These coated catheters can be used in, for example, cardiac catheterization, which is an important tool in the diagnosis and management of heart disease. Coated catheters can also be used in catheterization procedures to diagnose and treat various peripheral vascular disorders such as deep vein thrombosis. For the diagnosis and treatment of aneurysms intravascular catheterization is usually required. The procedures, which usually involve placement then threading of a catheter from a distant site, for example, from the femoral vein into the location of the aneurysm create a high risk of clot formation. A catheter having a surface coated with heparin-coupled microparticles in a matrix of polymeric material on the tip and along length of the catheter could protect against this occurrence. In yet another example, congenital and acquired vascular malformations could be treated as described above for aneurysms with the similar issue of clot and emboli formation.

Implantable medical devices coated with a matrix of polymeric material containing microparticles coupled to, or associated with, other pharmacologically active compounds can also be useful. Focal (or Partial) Epilepsy is the consequence of a localized area of abnormal chemical/electrical activity in the brain. Anticonvulsant medication is the most frequently used means of treating epilepsy. Mechanisms of action are believed to include either suppression of abnormal aberrant electrical activity or the prevention of spread of such activity and hence reduce the likelihood of the patient developing a clinical epileptic seizure. Anticonvulsant medication is usually given by mouth, absorbed from the bowel into the blood stream and then, to be effective, has to cross the blood-brain barrier. In order to cross the relatively impervious blood-brain barrier high doses must be given thereby increasing the likelihood of clinical toxicity and damage to other organs. The present invention can provide a mechanism for a more directed therapy. For example, microparticles could be coupled to, or associated with, anticonvulsant medication appropriate to the patient's epilepsy. Preferably, the medication is releasable from the microparticles over a desired period of time or pharmacologically active in its coupled form. A matrix of polymeric material including these pharmaceutical-coupled microparticles can be coated on the surface of a medically implantable device, for example a chip, and can be placed in the region of the brain that has been shown to be the site of seizure origin by techniques that are standard in the field of neurosurgery. In another example, Parkinson's Disease is a consequence of decreased dopamine in the neurons of the substantia nigra. Replacement therapy is often effective but side effects from the medication are common due to the need to provide these orally. The microparticles of the present invention could be coupled to, or associated with, or associated with dopamine or a precursor of dopamine and the matrix of polymeric material can be coated on the surface of a medically implantable device, for example a chip, and placed in the region of the brain that would supplement the diminishing or absent dopamine.

A number of cancers are treated by the administration of chemotherapeutic agents. Many of these agents used in systemic chemotherapy are toxic to other organ systems. Immobilization of microparticles coupled to, or associated with, a chemotherapeutic agent in a matrix of polymeric material on the surface of a medically implantable device can be placed at the site of the tumor, for example, in the abdominal, pelvic, or intracranial regions, and can provide direct chemotherapy to the site avoiding many of the systemic side-effects of this treatment. This can be useful in regions were cancer is often localized in the early stages, for example, at the prostate, testis, liver, or colon.

A number of infectious diseases require the sustained administration of antibiotics or antiviral medications. Antibiotics often do not easily penetrate the inflamed or fibrous tissue that surrounds the region of active infection in an abscess. In another application, antibiotics can be coupled to, or associated with, the microparticles of the invention and a mixture containing these microparticles and a polymeric material coated on a catheter or a similar device which is then placed around or within an abscess by standardized surgical techniques known to those skilled in the art. This would ensure a steady and sustained dosage of antibiotic while avoiding the systemic effects of the medication. Abscesses are often found in regions that are not easily accessible or have a limited blood supply such as within bone. Antibiotic administration can also be accomplished by coupling the microbeads to an appropriate antibiotic and coating the polymeric mixture containing microparticles on a substrate such as a catheter tip. Such a catheter may be placed in the region where an infectious process has been identified, for example, the bladder, and the antibiotic slowly released.

The invention contemplates methods for preparing surfaces coated with microparticles immobilized in a matrix, methods of delivering these compounds from these coated surfaces, and the surfaces themselves.

EXAMPLES

Example 1

Entrapment of Microparticles on a Substrate Using Via a Photopolymer Matrix

Microparticles were immobilized on the surface of a substrate by entrapment of the microparticles in a matrix of polymeric material. This method of immobilization does not interfere with the surface functionality of the microparticle since no chemical bonds were formed between the microparticle and matrix of polymeric material. Specifically, the microparticles do not provide any target groups with which the benzophenone of the photopolymer can react to form stable new bonds. Therefore, the surface chemistry on the microparticle is not altered. Covalent bonds between polymer molecules were formed after a mixture containing microparticle and polymeric material was coated on the device. Irradiation of the photopolymer crosslinked the polymer with itself encasing the microparticles, but did not alter the biomolecules attached to the microparticles.

To demonstrate this immobilization method, plain silica microparticles of four different diameters (0.4 μm, 0.9 μm, 5.0 μm, and 9.9 μm) were immobilized in photopolymer matrices of differing concentrations. At the lowest concentration of photopolymer the polymeric matrix formed was not sufficient to physically immobilize the microparticles of the sizes tested. As an additional control, some photopolymer coatings were not irradiated which resulted in insufficient crosslinking around the microparticle and leading to microparticle loss from the coating. Stringent rinses in detergent and high salt solutions at elevated temperatures were used to ensure that the photopolymer coatings were robust.

20 μl of 100 mg/ml aliquots of each 400 nm, 970 nm, 5 μm, and 9.9 μm silica microparticles solutions (cat. # SS02N, SS03N, SS05N, and SS06N, respectively; Bangs Laboratories, Fisher, Ind.) were pelleted by centrifugation. These pellets were individually resuspended in 100 μl serial dilutions of (BBA-APMA:VP)-I which is a copolymer of vinylpyrrolidone (VP) and N-[3-(4-Benzoylbenzamido)propyl]methacrylamide (BBA-APMA). The dilution series consisted of 10, 5, 2.5, 1.25, 0.6, 0.3, 0.15, 0.08, 0.04 and 0.02 mg/ml concentration samples of (BBA-APMA:VP)-I. The final concentration of microparticles was 20 mg/ml for all sizes. Therefore, the 400 nm microparticle solution contained significantly more microparticles than did the 9.9 μm microparticle solution; however all microparticle solutions contained the same percent solids.

Polypropylene and silanated glass slides (1×3 in.×1 mm) were used as substrates. Glass microscope slides were obtained from Erie Scientific, Portsmith, N.H. (catalog #2950-W). These soda lime glass microscope slides were silane treated by dipping in a mixture of 1% v/v p-tolyldimethylchlorosilane (T-Silane) and 1% v/v n-decyldimethylchlorosilane (D-Silane, United Chemical Technologies, Bristol, Pa.), each in acetone, for 1 minute. After air drying, the slides were cured in an oven at 120° C. for one hour. The slides were then washed with acetone followed by dipping in deionized water. The slides were further dried in an oven for 5-10 minutes. Polypropylene slides were prepared at and obtained from Cadillac Plastics (Minneapolis, Minn.). The silanated glass or polypropylene slides were then washed in acetone or isopropanol.

5 μl of each microparticle-(BBA-APMA:VP)-I solution was placed in an area of approximately 10 mm×2 mm on a glass slide and allowed to air dry. Once dry, the coatings were irradiated for two (2) minutes with broad spectrum ultraviolet light (320-390 nm) using a Dymax LightWelder PC-2 (Dymax Engineering Adhesives, Torrington, Conn.) having a typical power output of 2 mW/cm$^2$. The lamp was positioned approximately 10 cm from the coated surface. A second set of samples was not irradiated to serve as a control to determine whether crosslinking the photopolymer matrix was necessary to contain the microparticles.

To determine if the microparticles were entrapped well in the polymer coating, the coated slides were washed in a 1×PBS-0.1% Tween-20 solution with mild shaking for one hour, followed by two deionized water rinses. The coatings were then re-examined by microscope and the microparticle loss evaluated. A second wash condition of higher salt with higher temperature was then conducted. The microparticle coated pieces were incubated and shaken in 4×SSC buffer with 0.1% SDS for 45 minutes at 45° C., then rinsed twice with deionized water and examined microscopically for changes in the microparticle coating. Finally a longer high salt wash step was conducted, with the slides incubating in 5×SSC buffer with 0.1% SDS for two hours at 45° C., followed by four rinses of decreasing concentration of SSC. The microparticle coatings were examined by qualitative microscopic examination at 50× magnification (Olympus BX60, Tokyo, Japan) and the changes were tabulated. Results are shown in FIG. 2 and FIG. 3.

Figure 2A:
FIGS. 2a-2d are photomicrographs of microparticles immobilized within a polymeric matrix on a substrate.
Figure 2B:
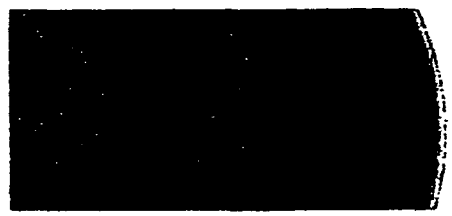
Figure 2C:
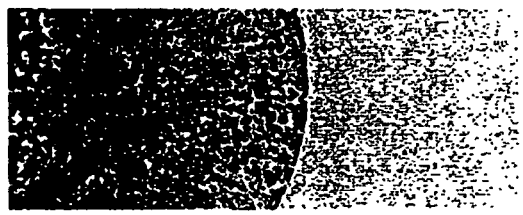
Figure 2D:
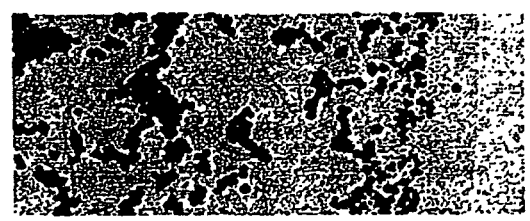

FIG. 2a-2d shows presence of the microparticles after the final wash. FIG. 2a shows a coating having 400 nm microparticles; FIG. 2b shows a coating having 970 nm microparticles; FIG. 2c shows a coating having 5 μm microparticles; and FIG. 2d shows a coating having 9.9 μm microparticles.

Figure 3A:
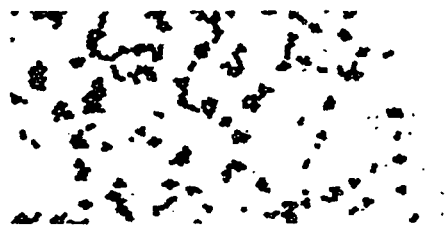
FIGS. 3a and 3b are photomicrographs of microparticles immobilized within a polymeric matrix on a substrate.
Figure 3B:
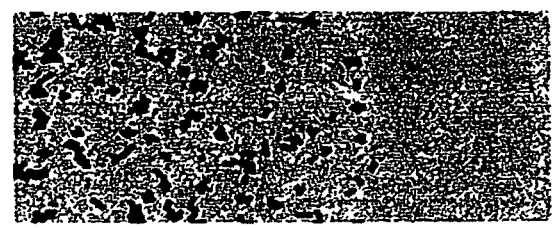
Figure 5:
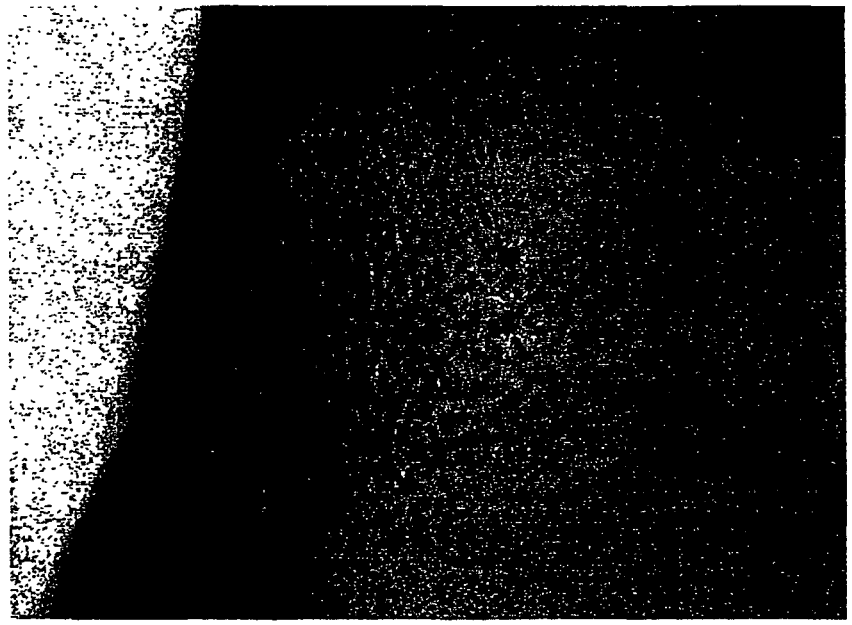
FIG. 5 is a photomicrograph of microparticles immobilized within a polymeric matrix on a polyurethane substrate.

A micrograph of microparticles before and after all three washes is shown in FIG. 3. FIG. 3a shows 9.9 μm microparticles in a 0.3 mg/ml (BBA-APMA:VP)-I matrix before washing and FIG. 3b shows 9.9 μm microparticles in a 0.3 mg/ml (BBA-APMA:VP)-I matrix after washing. The results are shown in Table 2 and Table 3. As indicated in Tables 2 & 3: N=No Loss, S=Slight Loss, M=Moderate Loss, H=Heavy Loss, C=Complete Loss; PBST=1×PBS-0.1% Tween-20 wash for one hour at room temperature; 4×SSC=4×SSC-0.1% SDS wash for 45 minutes at 45° C.; Final=5×SSC-0.1% SDS wash for two hours at 45° C.

TABLE 2

| | Irradiated | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| (BBA-APMA:VP)-I mg/ml | 10 | | | 5 | | | 2.5 | | | 1.25 | | | 0.6 | | | 0.3 | | | 0.15 | | | 0.08 | | | 0.04 | | | 0.02 | | |
| Wash Step | PBST | 4×SSC | Final | PBST | 4×SSC | Final | PBST | 4×SSC | Final | PBST | 4×SSC | Final | PBST | 4×SSC | Final | PBST | 4×SSC | Final | PBST | 4×SSC | Final | PBST | 4×SSC | Final | PBST | 4×SSC | Final | PBST | 4×SSC | Final |
| 400 nm | N | N | N | N | N | N | N | N | N | N | N | N | N | N | N | N | N | N | N | N | S | S | S | S | S | S | S | M | H | H | H | C | |
| 970 nm | N | N | N | N | N | N | N | N | N | N | N | N | N | N | N | N | N | N | N | N | S | S | S | S | S | S | S | H | C | | H | C | |
| 5 μm | N | N | N | N | N | N | N | N | N | N | N | N | N | N | N | N | N | N | S | S | S | S | M | M | M | H | H | M | H | H |
| 9.9 μm | N | N | N | N | N | N | N | N | N | N | N | N | N | N | N | N | N | N | S | S | S | S | M | M | M | H | H | M | H | H |

TABLE 3

| (BBA-APMA:VP)-I mg/ml | 10 | | | 5 | | | 2.5 | | | 1.25 | | | 0.6 | | | 0.3 | | | 0.15 | | | 0.08 | | | 0.04 | | | 0.02 | | |
|---|---|---|---|---|---|---|---|---|---|---|---|---|---|---|---|---|---|---|---|---|---|---|---|---|---|---|---|---|---|---|
| | Non-Irradiated | | | | | | | | | | | | | | | | | | | | | | | | | | | | | |
| Wash Step | PBST | 4XSSC | Final | PBST | 4XSSC | Final | PBST | 4XSSC | Final | PBST | 4XSSC | Final | PBST | 4XSSC | Final | PBST | 4XSSC | Final | PBST | 4XSSC | Final | PBST | 4XSSC | Final | PBST | 4XSSC | Final | PBST | 4XSSC | Final |
| 400 nm | M | C | | M | C | | M | C | | M | C | | M | C | | M | C | | | C | | H | C | | | C | | | C | |
| 970 nm | M | C | | M | C | | M | C | | M | C | | M | C | | M | C | | | C | | H | C | | H | C | | | C | |
| 5 μm | M | C | | M | C | | M | C | | M | C | | M | C | | M | C | | | C | | M | C | | M | C | | | C | |
| 9.9 μm | M | C | | M | C | | M | C | | M | C | | M | C | | M | C | | H | C | | H | C | | H | C | | H | C | |

As shown above in Tables 2 and 3, microparticle loss was significantly increased in samples that had not been irradiated. Also shown above in Tables 2 and 3, microparticle loss was increased when the concentration of polymer was reduced. Microparticle loss was increased when a smaller size of microparticle was used in the matrix of polymeric material. This data indicates that irradiation promoted the formation of an encasing polymeric network around the microparticles. This data also indicates that the microparticles were immobilized by physical constraints of the matrix of polymeric material rather than by chemical bonding.

When coated on a substrate the slurries having smaller microparticles gave coatings that densely packed with multiple layers of microparticles, whereas slurries with larger microparticles gave coatings had loosely arranged microparticles every few tenths of a millimeter. Coatings showing the lower density of microparticles were as stable to the wash conditions as ones with dense concentrations.

Example 2

Patterned Coatings of Microparticles Entrapped Via a Photopolymer Matrix on a Substrate In this example, coated substrates were created using the procedure of Example 1 with decreasing concentrations of photoreactive polymer but with a patterned coating of the photopolymer. At lower concentrations of photoreactive polymer, the polymeric matrix no longer held the microparticles in place following a mild rinse.

Slurries of 5 mg/mL (BBA-APMA:VP)-I were serially diluted to 2.5, 1.25, 0.625, 0.313 mg/mL in deionized water and a solution of 0.25 mg/mL of 1.0 μm fluorescent polystyrene microparticles (Bangs Laboratories, Fisher Ind.) was added to each dilution. 45 μl of each of the serially diluted (BBA-APMA:VP)-I solutions were added to 5 μl of 40 mg/ml microparticles in deionized water to create slurries where the final concentration of microparticles is 4 mg/ml in each mixture of 50 μl total.

The slurries were all contact printed on a Microgrid II arrayer (Biorobotics, Cambridge, UK) and then irradiated for two minutes with ultraviolet light as detailed in Example 1 (Dymax LightWelder PC2, Dymax Engineering Adhesives, Torrington, Conn.) through a 315 nm cutoff filter (Electro-Lite Corporation, Danbury, Conn.). The coated substrates were then rinsed three times with 1×PBS with 0.1% Tween-20 and with deionized water. The resulting spots were imaged with a fluorescence microscope (Olympus BX 60, Tokyo, Japan) using 100× magnification. As shown in FIG. 4, the (BBA-APMA:VP)-I polymeric matrix immobilized the microparticles until the concentration dropped below 0.625 mg/mL (FIG. 4d), when the microparticles were rinsed free from the polymeric matrix. FIG. 4a shows microparticles immobilized in 5 mg/mL (BBA-APMA:VP)-I; FIG. 4b shows microparticles immobilized in 2.5 mg/mL (BBA-APMA:VP)-I, FIG. 4c shows microparticles immobilized in 1.25 mg/mL (BBA-APMA:VP)-I, FIG. 4d shows microparticles immobilized in 0.625 mg/mL (BBA-APMA:VP)-I, FIG. 4e shows microparticles immobilized in 0.313 mg/mL mg/mL (BBA-APMA:VP)-I.

Example 3

Entrapment of Heparin-Coated Microparticles on a Substrate Using Via a Photopolymer Matrix Surfaces or substrates can be coated with slurries containing polymeric material and microparticles coupled to, or associated with, an agent or agents and therefore can provide a surface with an agent, for example, a biologically active agent. For example, immobilizing heparin-coated microparticles in a hydrophilic polymeric matrix can provide anticoagulant activity to a surface, making such a microparticles-polymer coating suitable for medical device applications that require blood compatibility.

In this example, streptavidin-coated microparticles were coupled to a biotinylated albumin-heparin conjugate to create heparin-coated microparticles. These microparticles were then entrapped in a hydrogel of photoreactive poly(vinylpyrrolidone) and coated onto a polyurethane rod. The coated polyurethane rod can be used in medical devices. The coated rod was stable to wash conditions and the microparticles could be detected both via microscopic analysis and by staining with Toluidine Blue 0 dye which detects the sulfonate groups on heparin.

10 mg of 5.23 μm streptavidin-coated silica microparticles (CS01N, Bangs Laboratories, Fisher, Ind.) was washed with 900 μl of 1×PBS, centrifuged to pellet the microparticles, and then resuspended in a solution of 35 μg/ml biotinylated albumin-heparin (H-4016, Sigma, St. Louis, Mo.) in 1×PBS. This reaction mixture was incubated overnight with end-over-end mixing, after which the microparticles were washed twice with 1 ml of PBS, pelleted and resuspended in 150 μl of 50 mg/ml (BBA-APMA:VP)-I in deionized water. The final coating solution consisted of 66.7 mg/ml of heparin-coated microparticles and 50 mg/ml (BBA-APMA:VP)-I.

A 2-inch long, 0.118-inch in diameter, piece of polyurethane rod (Tecoflex EG-60D; Thermedics Polymer Products, Woburn, Mass.) was cleaned with an isopropanol rinse, rinsed twice with deionized water, and air dried. The rod was then coated by dipping one end in the above coating solution to a depth of approximately 1 cm and then drying at 45° C. The polymeric matrix on the rod was irradiated for two minutes on each side with an ultraviolet light source as detailed in Example 1 (LightWelder PC-2, Dymax Engineering Adhesives, Torrington, Conn.) and rinsed with deionized water. The above coating procedure was performed three additional times. The polyurethane rod contained four coats of the heparin-coated microparticle (BBA-APMA:VP)-I coating. After the final water rinse the rod was imaged microscopically (Olympus BX60, Tokyo, Japan) at 50× and 200× magnification, as shown in FIG. 1.

The heparin coating on the polyurethane rod was also examined by staining with Toluidine Blue O dye (19816-1, Aldrich, Milwaukee, Wis.). The rod was placed in a solution of 0.02% w/v Toluidine Blue (TBO) in deionized water in a test-tube for ten minutes at room temperature. The TBO staining solution was removed by aspiration and the rod was washed twice with 2 ml of deionized water. The stained rod was transferred to a clean test-tube and 500 µl of 8M urea in 50 mM TRIS buffered saline was added. This solution was incubated for 15 minutes at room temperature and served to remove the TBO dye from the stained rod. The absorbance of the resulting urea solution was measured at 650 nm and indicated the amount of stain adsorbed by the rod. The higher the absorbance, the more dye stained the rod, and consequently more heparin on the rod surface. Controls were also stained in the above manner, including cleaned uncoated polyurethane rod, polyurethane rod coated with only the 50 mg/ml (BBA-APMA:VP)-I solution, and polyurethane rod coated with the above microparticle-(BBA-APMA:VP)-I solution where the microparticles had not been coupled to the biotinylated heparin-albumin, but had only the initial streptavidin coating. Results are summarized in Table 4, showing the heparin-coated microparticles stained significantly, while all control coatings stained minimally. This example demonstrates a simple heparin coated surface using the gel entrapment technology.

TABLE 4

| Substrate | $A_{650}$ nm |
|---|---|
| Uncoated Polyurethane Rod | 0.047 |
| Polyurethane rod coated with (BBA-APMA:VP)-I only | 0.067 |
| Polyurethane rod coated with streptavidin-coated microparticles in (BBA-APMA:VP)-I | 0.072 |
| Polyurethane rod coated with heparin-coated microparticles in (BBA-APMA:VP)-I | 1.051 |

Example 4

Entrapment of Microparticles by Disposing on a Photopolymer Matrix

Different polymeric materials were used to immobilize microparticles on a substrate. First, different polymers were disposed and treated on a substrate to form matrices. This was followed by disposing the microparticles on the substrates which were immobilized via the matrices. Four different photoreactive polymers were used to immobilize 9.9 µm diameter silica microparticles on substrates. (BBA-APMA:AA)-I and (BBA-APMA:AA)-II are copolymers of acrylamide (AA) and N-[3-(4-Benzoylbenzamido)propyl]methacrylamide (BBA-APMA) with differing ratios of BBA-APMA:AA. Similarly (BBA-APMA:VP)-I and (BBA-APMA:VP)-II are copolymers of vinylpyrrolidone (VP) and N-[3-(4-Benzoylbenzamido)propyl]methacrylamide (BBA-APMA) with differing ratios of BBA-APMA:VP. Additionally a control material, BBDQ which is (ethylene(4-benzoylbenzyldimethylammonium)dibromide; described in U.S. Pat. No. 5,714,360 to Swan et al., issued 3 Feb., 1998, commonly owned by the assignee of the present invention, the disclosure of which is incorporated herein in its entirety), a non-polymeric photoreactive compound, was evaluated.

Each photoreactive compound was dissolved in deionized water at a concentration of 2.5 mg/ml. Each solution was printed with 25 gauge disposable needles (PrecisionGlide Needles, Becton Dickinson and Co., Franklin Lakes, N.J.) and an x-y programmable stage (CAMM-3, Roland Digital Group, Irvine, Calif.) onto glass microscope slides which had been functionalized with silanes, as in Example 1, and onto acrylic slides (Cadillac Plastics, Minneapolis, Minn.). This printing forms a pattern of approximately 300-400 µm diameter spots on the substrates.

The patterned slides were irradiated for two minutes with ultraviolet light as detailed in Example 1. After irradiation, 500 µl of an aqueous solution of 2 mg/ml 9.9 µm diameter silica microparticles (SS06N, Bangs Laboratories, Fisher, Ind.) was placed over the patterned area for one minute to allow the microparticles to associate and become entrapped in the polymer matrices. The slides were then rinsed with 0.1% v/v Tween-20 aqueous solution to remove any free microparticles.

Following this, the array was washed to remove loosely bound microspheres. The array was washed three times with 1×PBS (pH 7.4) with 0.1% v/v Tween-20, and then rinsed with deionized water. At this point, each was imaged with a fluorescence microscope (Olympus BX 60, Tokyo, Japan), to determine microsphere loss in the various photoreactive polymer matrices. After imaging, the arrays were incubated in a solution of 0.1M TRIS and 50 mM ethanolamine (T/E) wash buffer for 1 hour at 50° C., followed by two rinses with deionized water. The microarrays were then incubated in a solution of 4×SSC/0.1% SDS for two hours at 50° C. and rinsed in deionized water. This was the final step at which imaging was done to evaluate the respective polymers. Results are summarized in Table 5.

TABLE 5

| Photoreactive Compound | Substrate | Presence of microparticles before washes | Presence of microparticles after PBS-Tween wash | Presence of microparticles after high salt wash (4X SSC) |
|---|---|---|---|---|
| (BBA-APMA:AA)-I | Glass | Present | Some loss | Significant loss |
| (BBA-APMA:AA)-I | Acrylic | Present | Some loss | No loss |
| (BBA-APMA:AA)-5 | Glass | Present | Some loss | No loss |

TABLE 5-continued

| Photoreactive Compound | Substrate | Presence of microparticles before washes | Presence of microparticles after PBS-Tween wash | Presence of microparticles after high salt wash (4X SSC) |
|---|---|---|---|---|
| (BBA-APMA:AA)-5 | Acrylic | Present | No loss | Some loss * |
| (BBA-APMA:VP)-I | Glass | Present | No loss | No loss |
| (BBA-APMA:VP)-I | Acrylic | Present | No loss | No loss |
| (BBA-APMA:VP)-II | Glass | Present | No loss | No loss |
| (BBA-APMA:VP)-II | Acrylic | Present | No loss | No loss |
| BBDQ - non-polymer control | Glass | Present | Some loss | Complete loss |
| BBDQ - non-polymer control | Acrylic | Present | Some loss | Complete loss |

* Sample was touching another slide during the wash.

Example 5

Printed Coatings of Microparticles Entraped Via a Photopolymer Matrix on a Substrate Slurries were prepared, each containing different polymers and microparticles. These slurries were then disposed on a substrate and treated to form matrices in which microparticles were immobilized. Different polymeric materials were used to immobilize microparticles on a substrate. Four different photoreactive polymers were used to immobilize 9.9 µm diameter silica microparticles on substrates: (BBA-APMA:AA)-I, (BBA-APMA:AA)-5, (BBA-APMA:VP)-I, and (BBA-APMA:VP)-II. BBDQ (as described in Example 4) a non-polymeric photoreactive material was also used in this Example.

(BBA-APMA:AA)-I, (BBA-APMA:AA)-5, (BBA-APMA:VP)-I, (BBA-APMA:VP)-II, and BBDQ were dissolved in deionized water at a concentration of 2.5 mg/ml. 100 µl of each solution containing photoreactive compound was added to a pellet of 2 mg of 9.9 µm diameter silica microspheres (SS06N, Bangs Laboratories, Fisher, Ind.) that had been washed three times with deionized water, to create a mixture. The final concentration of each mixture was 2.5 mg/ml of photoreactive compound and 20 mg/ml of microspheres. Each mixture was printed with 25 gauge disposable needles (PrecisionGlide Needles, Becton Dickinson and Co., Franklin Lakes, N.J.) and an x-y programmable stage (CAMM-3, Roland Digital Group, Irvine, Calif.) onto glass microscope slides which had been functionalized with silanes, as detailed in Example 1 and onto acrylic slides (Cadillac Plastics, Minneapolis, Minn.). This printing forms a pattern of approximately 300-400 µm diameter spots on the substrates.

The coated substrates were irradiated for two minutes with ultraviolet light as detailed in Example 1. The coated substrates were then imaged with a fluorescence microscope (Olympus BX 60, Tokyo, Japan), to ensure that patterning was successful.

Following this, the coated substrate was washed to remove any loosely bound microspheres. The coated substrates were washed three times with 1×PBS (pH 7.4) with 0.1% v/v Tween-20, rinsed with deionized water. At this point, each was again imaged with the fluorescence microscope to determine microsphere loss in the various photoreactive polymer matrices. After imaging, the coated substrates were incubated in a solution of T/E wash buffer for 1 hour at 50° C., followed by two rinses with deionized water. The coated substrates were then incubated in a solution of 4×SSC/0.1% SDS for two hours at 50° C. and rinsed in deionized water. The presence of the microparticles before and after washing steps is summarized in Table 6.

TABLE 6

| Photoreactive Compound | Substrate | Presence of microparticles before washes | Presence of microparticles after PBS-Tween wash | Presence of microparticles after high salt wash (4X SSC) |
|---|---|---|---|---|
| (BBA-APMA:AA)-I | Glass | Present | No loss | No loss |
| (BBA-APMA:AA)-I | Acrylic | Present | No loss | No loss |
| (BBA-APMA:AA)-5 | Glass | Present | No loss | No loss |
| (BBA-APMA:AA)-5 | Acrylic | Present | No loss | Some loss * |
| (BBA-APMA:VP)-I | Glass | Present | No loss | No loss |
| (BBA-APMA:VP)-I | Acrylic | Present | No loss | No loss |
| (BBA-APMA:VP)-II | Glass | Present | No loss | No loss |
| (BBA-APMA:VP)-II | Acrylic | Present | No loss | No loss |
| BBDQ - non-polymer control | Glass | Present | No loss | Complete loss |
| BBDQ - non-polymer control | Acrylic | Present | No loss | Complete loss |

* Sample was touching another slide during the wash.

Example 6

Preparation of Substrates Having a Coating of Magnetic Resonance-Detectable Microparticles in a Polymeric Matrix Microparticles associated with paramagnetic iron oxide can be detected by paramagnetic resonance imaging (MRI) techniques. Therefore, coatings including immobilized paramagnetic microparticles can allow the imaging of medical devices in the body during, for example, surgical procedures or in vivo device monitoring. Microspheres functionalized with iron oxide are commercially available in a variety of sizes from, for example, Bangs Laboratories (Fishers, Ind.) and can be used in this application.

1 μm diameter paramagnetic polystyrene microspheres (CM01F, Bangs Laboratories, Fisher, Ind.) can be washed with deionized water three times and then resuspended in fresh deionized water. Following the washing, the pellet of 10 mg of microspheres can be resuspended in 250 μl of 50 mg/ml (BBA-APMA:VP)-I to create a mixture for coating a substrate. A medical device or medical device substrate, comprised of a material such as low density polyethylene or polyurethane, can then be dipcoated with the mixture of paramagnetic microspheres in photoreactive polymer. Following air drying, the coated piece can be irradiated with ultraviolet light as detailed in Example 1, for at least two minutes. This irradiation can serve to form the matrix around the microspheres entrapping them as well as covalently bonding the polymeric material to the medical device substrate.

The paramagnetic coating can be evaluated either directly by MRI, or by examining the Ti lifetime of the iron oxide particles associated with the microparticles on the surface of the device with an NMR spectrometer, such as a 400 MHz Brueker NMR. A positive signal can be observed as a dark contrast to bodily fluid.

Example 7

Alternative Methods for Preparation of Substrates Having a Coating of Magnetic Resonance-Detectable Microparticles in a Polymeric Matrix Paramagnetic iron oxide microparticles can also be prepared by the user and detected by paramagnetic resonance imaging (MRI) techniques.

Paramagnetic iron oxide microparticles can be created by precipitation of a mixture of ferrous and ferric chloride salts with concentrated ammonium hydroxide aqueous solutions. After precipitation the paramagnetic microparticles can be purified by dialysis to remove unwanted salts and base. The microparticles can then be concentrated by vacuum drying. Drying may cause the microparticles to clump together slightly which should increase the average size without loss of magnetism. The paramagnetic iron oxide microparticles at a concentration in the range of 0.1 to 5 mg/ml can be incorporated into a mixture of photoreactive polyvinylpyrrolidone ((BBA-APMA:VP)-I or (BBA-APMA:VP)-II. The mixture would include (BBA-APMA:VP)-I or (BBA-APMA:VP)-II at a higher concentration, in the range of 1 to 40 mg/ml, with the optional addition of a water soluble photoreactive crosslinker such as BBDQ, as detailed in Example 4. Smaller ferric oxide microparticles, for example, in the range of 1 to 50 nm in diameter, may require additional crosslinking of the photopolymer matrix to minimize pore size. Additional crosslinker can be added in the range of 0.1 to 5 mg/ml in the final mixture of photoreactive polymer, ferric oxide microparticles, and crosslinker. The mixture coating can be applied by dipping the medical device to be coated, or medical device substrate, for example, a low density polyethylene, into the mixture and air drying. The coating can be irradiated for at least two minutes with ultraviolet light as detailed in Example 1. Once coated the device or device substrate can be rinsed with deionized water and phosphate buffered saline with 0.1% v/v Tween-20. The coated pieces can be tested for paramagnetic resonance imaging signal by either evaluating the Tl signal lifetime with a nuclear paramagnetic resonance spectrometer (NMR) or by imaging directly with an MRI machine.

Example 8

Preparation of a Substrate Coated with Dexamethasone-PLGA Microparticles in a Polymeric Layer and Release of Dexamethasone from the Surface Degradable microspheres were prepared containing an anti-inflammatory agent and then immobilized on a substrate surface in a polymeric matrix. The microsphere-coated substrate was then placed in media and the release of the anti-inflammatory agent from the surface of the substrate was quantified over a period of time.

Poly(lactide-co-glycolide) (PLGA) microspheres loaded with dexamethasone were prepared by an oil-in-water emulsion/solvent evaporation technique (Wichert, B. and Rohdewald, P. (1993) *J. Microencapsul.* 10:195). The oil phase consisted of 20 mg of dexamethasone (Aldrich, St. Louis, Mo.) and 100 mg of PLGA (50:50 lactide:glycolide; average MW 50,000-75,000; Aldrich, St. Louis, Mo.) dissolved in 5 ml of 9:1 dichloromethane:methanol. This oil phase was added dropwise to 100 ml of 0.2% (w/v) aqueous polyvinyl alcohol (PVA) solution (Aldrich, St. Louis, Mo.) under vigorous stirring with a Caframo mechanical stirrer (Model RZR 1; VWR Scientific, Chicago, Ill.) for 30 minutes on stir setting #4. The stirring was then reduced to the lowest setting and the organic solvent was allowed to evaporate at room temperature for 16 hr. The PVA mixture containing the formed dexamethasone-PLGA microparticles was centrifuged at 8000 rpm to pellet the microparticles. The microparticles were washed twice with deionized water and lyophilized. 74 mg of microparticles were recovered (74% yield). To ascertain the dexamethasone loading of the microparticles, 2.5 mg of microparticles were dissolved in 5 ml of 9:1 dichloromethane:methanol and the absorbance measured at 250 nm on a Shimadzu spectrophotometer (Model UV-1601, Columbia, Md.). The microparticles were determined to contain 5.85% (w/w) dexamethasone.

A slurry of the 10 mg dexamethasone-PLGA microparticles in 400 μL of 2 mg/ml aqueous solution of photoreactive poly(vinylpyrrolidone) copolymer (BBA-APMA:VP)-II, was prepared, and the slurry was cast on a approximately half the area of a 1"×3" polystyrene sheet (Goex Plastics, Janesville, Wis.). The film formed on the polystyrene sheet was allowed to dry for one hour at room temperature followed by irradiation with UV light (Dymax, Light-Welder PC-2, Torrington, Conn.) for four minutes. The coated polystyrene sheet was then immersed in 20 ml of 10 mM phosphate buffered saline, pH=7.4 and shaken at 37° C. for a predetermined period of time on a Scienceware Spindrive orbital shaker (Pequannock, N.J.). The buffered medium was completely removed and the polystyrene sheet was rinsed with water. The buffered medium and the rinse water were collected, combined, and subject to rotary evaporation. The evaporated residue in the flask was extracted with 5 ml of dichloromethane:methanol (90:10) mixture at room temperature. The UV absorbance of dichloromethane:methanol extract was measured at 250 nm to quantify the amount of dexamethasone released during the time allowed to soak in the buffered media. The polystyrene sheet was then immersed in 20 ml of fresh buffer medium and the process repeated for quantification of the drug release over three weeks. The amount of dexamethasone (DEX) released from the beads over time is shown in Table 7.

TABLE 7

| Time (hr) | Cumulative DEX Release (mg) | Cumulative DEX Release (%) |
| --- | --- | --- |
| 1 | 0.2508 | 42.50 |
| 6 | 0.2764 | 46.85 |
| 30 | 0.2959 | 50.16 |
| 54 | 0.3072 | 52.06 |
| 150 | 0.3172 | 53.75 |
| 318 | 0.3705 | 62.80 |
| 870 | 0.5067 | 85.88 |
| 990 | 0.7182 | 121.73 |

TABLE 8

| Time (hr) | CHD Released (mg) | CHD Released (%) |
| --- | --- | --- |
| 1 | 0.206 | 37.4 |
| 18 | 0.289 | 52.3 |
| 42 | 0.318 | 57.6 |
| 66 | 0.338 | 61.2 |
| 162 | 0.358 | 64.8 |
| 330 | 0.378 | 68.4 |
| 882 | 0.626 | 113.5 |
| 1002 | 0.869 | 157.4 |

Example 9

Preparation of a Substrate Coated with Chlorhexidine-PLGA Microparticles in a Polymeric Layer and Release of Chlorhexidine from the Surface Microspheres were prepared containing an anti-microbial agent and then immobilized on a substrate surface in a polymeric material as described in Example 8. The microsphere-coated substrate was then placed in media and the release of the anti-microbial agent from the surface of the substrate was quantified over a period of time.

Poly(lactide-co-glycolide) (PLGA) microspheres containing 3.95% chlorhexidine diacetate were prepared following the same oil-in-water/solvent evaporation technique described in Example 8 with slight modification. The oil phase was prepared containing 58 mg of chlorhexidine diacetate (ICN Biomedicals, Aurora, Ohio) and 300 mg of PLGA in 10 ml of dichoromethane:methanol (90:10) mixture. The oil phase was added dropwise to 100 ml of 0.2% (w/v) polyvinyl alcohol (PVA) in 20 mM phosphate buffered saline under vigorous stirring. The organic solvent was allowed to evaporate over 16 hr while the mixture was stirred at room temperature. The mixture containing the formed chlorhexidine-PLGA microparticles was centrifuged at 8000 rpm to pellet the microparticles. The microparticles were washed multiple times with deionized water and lyophilized. 210 mg of microparticles were recovered having a chlorhexidine content of 3.95% (w/w) as determined by dissolution of the microparticles in 9:1 dichloromethane:methanol and measurement of the UV absorbance of chlorhexidine at 260 nm. Light microscopy with a Leica Model DMLM microscope (Wetzler, Germany) showed particle sizes ranging from 24 to 52 μm diameter.

The process of casting the photoreactive polymer films with the chlorhexidine-loaded particles and the determination of drug release are the same as described in Example 8. A slurry of 13.8 mg of chlorhexidine loaded PLGA particles in 400 μl of 1 mg/ml photoreactive poly(vinylpyrrolidone) copolymer (PV05) was cast on a 1"×3" polystyrene sheet. The microparticle coating was dried for one hour at room temperature and fixed in place by irradiating for four minutes with ultraviolet light as in Example 8. The chlorhexidine release from the coating was monitored by ultraviolet absorbance at 260 nm in a similar manner to Example 8. The amount of chlorhexidine diacetate released from the beads over time is shown in Table 8.

Example 10

Preparation of a Substrate Coated with Chlorhexidine-Chitosan Microparticles in a Polymeric Layer and Release of Chlorhexidine from the Surface Degradable chitosan microspheres were prepared containing an anti-microbial agent and then immobilized on a substrate surface in a polymeric material as described in Example 8. The microsphere-coated substrate was then placed in media and the release of the anti-microbial agent from the surface of the substrate was quantitated over a period of time.

Chlorhexidine diacetate-loaded chitosan particles were prepared by a spray drying procedure. In this experiment, 1.0 gm of chlorhexidine diacetate (ICN Biomedicas, Aurora, Ohio) was dissolved in one liter of chitosan solution (0.5%, w/v) (Aldrich, St. Louis, Mo.) in 0.03 N hydrochloric acid and then spray dried in a LabPlant Model SD-05 spray-dryer (Huddersfield, W. Yorkshire, UK). The chlorhexidine loading is calculated at 20% (w/w).

The process of casting the photoreactive polymer films with the chlorhexidine-loaded particles and the kinetic determination of drug release are the same as described in Example 8. 11 mg of chlorhexidine-loaded chitosan microparticles were dispersed in 600 μl of 1.4 mg/ml photoreactive poly(vinylpyrrolidone) copolymer (BBA-APMA:VP)-II and cast onto a 1"×3" polystyrene sheet. The coated polystyrene was irradiated for four minutes with an ultraviolet lamp (Dymax, Light-Welder PC-2, Torrington, Conn.) to fix the microparticles in place. The drug release from the coating was monitored by extraction into aliquots of 20 ml of PBS buffer solution as in Example 8. The absorbance of chlorhexidine diacetate at 260 nm was used for quantification. The amount of chlorhexidine diacetate released from the beads over time is shown in Table 9.

TABLE 9

| Time (hr) | CHD Released (mg) |
| --- | --- |
| 1 | 0.31 |
| 18 | 0.60 |
| 42 | 0.84 |
| 114 | 1.05 |
| 210 | 1.24 |
| 282 | 1.32 |
| 378 | 1.44 |
| 450 | 1.58 |
| 618 | 1.71 |

Example 11

Preparation of a Substrate Coated with Chlorhexidine-Glass Microparticles in a Polymeric Layer and Release of Chlorhexidine from the Surface Non-degradable porous glass microspheres were prepared containing an anti-microbial agent and then immobilized on a substrate surface in a polymeric material as described in Example 8. The microsphere-coated substrate was then placed in media and the release of the anti-microbial agent from the surface of the substrate was quantified over a period of time.

A mixture of silica beads having diameters in the range of 2 to 25 μm, an average pore size of 600 nm, and an average pore volume of 0.75 cc/g (Bangs Laboratories; Fisher, Ind., USA) were washed repeatedly with water and dispersed in ethanol. 300 mg of beads dispersed in ethanol were mixed with 108.5 mg of chlorhexidine diacetate in 5 ml absolute ethanol and stirred for 16 hr at room temperature. The ethanol was evaporated and the particles dried at room temperature. The chlorhexidine-impregnated glass beads, 30 mg, were mixed with 300 μl of 1.33 mg/ml of photoreactive polymer, (BBA-APMA:VP)-II, prepared in 0.1 M phosphate buffered saline (PBS), pH 7.4. The bead-polymer mixture was cast on a silanized glass slide (prepared as described in Example 1), dried for one hour at room temperature, and then cured using a UV light source (Dymax, Light-Welder PC-2) for 4 minutes. The intensity of the UV light from a 2 inch long medium pressure (200 Watts/inch) iron doped mercury vapor bulb was 1.4 mWatt/cm$^2$ at 20 cm distance from the bulb. The coated glass slide was then immersed in 20 ml of 10 mM phosphate buffered saline, pH=7.4, and was shaken at 37° C. for a predetermined period of time. The buffer medium was completely removed and the glass slide was rinsed with water. The buffered medium and the rinse water were collected, combined, and subject to rotary evaporation. The evaporated residue in the flask was extracted with 5 ml of dichloromethane:methanol (90:10) mixture at room temperature. The UV absorbance of dichloromethane:methanol extract was measured at 260 nm to quantify the amount of chlorhexidine released during the time allowed to soak in the buffer medium. The glass slide was immersed in 20 ml of fresh buffer medium and release of chlorhexidine was quantified over time until no further release could be detected. The amount of chlorhexidine diacetate released from the beads over time is shown in Table 10.

TABLE 10

| Time (hr) | CHD Released (mg) |
|---|---|
| 1 | 0.48 |
| 19 | 0.82 |
| 43 | 1.26 |
| 115 | 1.49 |
| 211 | 1.75 |
| 283 | 1.99 |
| 379 | 2.14 |
| 451 | 2.20 |
| 547 | 2.29 |
| 619 | 2.54 |
| 715 | 2.66 |

What is claimed is:

1. An implantable medical device comprising:
   a) a surface;
   b) a matrix comprising polymeric material, the matrix polymeric material comprising a hydrophobic polymer, copolymer or combinations thereof, and one or more photoreative groups covalently attached to the matrix polymeric material, and wherein the matrix polymeric material is covalently attached to the surface by the photoreactive groups; and
   c) a plurality of microparticles immobilized in the matrix of polymeric material, wherein the microparticles comprise a biologically active agent, and the microparticles are 100 nm to 20 μm in diameter, and wherein the biologically active agent is released from the matrix in the presence of a fluid-containing environment.

2. The implantable medical device of claim 1 that is an intravascular catheter.

3. The implantable medical device of claim 1 wherein the surface comprises a balloon.

4. The implantable medical device of claim 1 wherein the microparticles comprise an antiproliferative agent.

5. The implantable medical device of claim 1 wherein some microparticles are associated with the matrix although not completely surrounded by polymeric material.

6. The implantable medical device of claim 1 wherein the microparticles are degradable.

7. The implantable medical device of claim 1 wherein the microparticles are formed by solvent evaporation.

8. The implantable medical device of claim 1 wherein the photoreactive group is selected from the group consisting of aryl ketones, arylazides, acyl azides, sulfonyl azides, phosphoryl azides, diazoalkanes, diazoketones, diazoacetates, and ketenes.

9. The implantable medical device of claim 1 wherein the polymer, copolymer, or combinations thereof, comprises a synthetic hydrophobic polymer.

10. The implantable medical device of claim 9 wherein the polymer, copolymer, or combinations thereof, is selected from the group consisting of polyacrylamide, polymethacrylamide, polyvinylpyrrolidone, polyacrylic acid, polyethylene glycol, polyvinyl alcohol, and poly(HEMA), copolymers thereof, and combinations thereof.

11. The implantable medical device of claim 1 wherein the microparticles are immobilized in the matrix by entrapment, wherein the entrapment of the microparticles does not depend on the formation of ionic or covalent bonds between the microparticles and the polymeric material.

12. The implantable medical device of claim 1 wherein the matrix has a thickness and the microparticles have a diameter and the thickness of the layer is greater than the diameter of the microparticles.

13. The implantable medical device of claim 1 wherein a plurality of compounds smaller than the microparticles are diffusible in the matrix of polymeric material.

14. The implantable medical device of claim 1 wherein the matrix comprises a polymer crosslinking compound.

15. The implantable medical device of claim 14 wherein the polymer crosslinking compound comprises at least one photoactivatable group.

16. The implantable medical device of claim 1 formed by disposing a polymer comprising photoreactive groups on the surface, treating the polymer to form the matrix, and then disposing the plurality of microparticles on the matrix, wherein the microparticles become immobilized in the matrix.

* * * * *